(12) United States Patent
Namii et al.

(10) Patent No.: US 7,768,701 B2
(45) Date of Patent: Aug. 3, 2010

(54) THREE-DIMENSIONAL MEDICAL IMAGING APPARATUS

(75) Inventors: Yasushi Namii, Hachioji (JP); Kenji Hirose, Hachioji (JP); Koji Yasunaga, Hino (JP)

(73) Assignee: Olympus Corporation, Tokyo (JP)

(*) Notice: Subject to any disclaimer, the term of this patent is extended or adjusted under 35 U.S.C. 154(b) by 0 days.

(21) Appl. No.: 12/287,616

(22) Filed: Oct. 9, 2008

(65) Prior Publication Data

US 2009/0054765 A1    Feb. 26, 2009

Related U.S. Application Data

(62) Division of application No. 11/288,339, filed on Nov. 29, 2005, now Pat. No. 7,453,631.

(30) Foreign Application Priority Data

Dec. 2, 2004    (JP) .............................. 2004-350265

(51) Int. Cl.
*G02B 21/22* (2006.01)
(52) U.S. Cl. ...................................... 359/377
(58) Field of Classification Search ................. 359/376, 359/377, 378, 380, 381; 600/111, 166
See application file for complete search history.

(56) References Cited

U.S. PATENT DOCUMENTS

| | | | |
|---|---|---|---|
| 5,557,454 A | 9/1996 | Takahashi | |
| 6,317,260 B1 * | 11/2001 | Ito | ............................... 359/377 |
| 6,327,079 B1 | 12/2001 | Namii et al. | |
| 6,525,878 B1 * | 2/2003 | Takahashi | .................... 359/466 |
| 2002/0082476 A1 | 6/2002 | Takahashi et al. | |

FOREIGN PATENT DOCUMENTS

| | | |
|---|---|---|
| JP | 06-202006 | 7/1994 |
| JP | 07-261099 | 10/1995 |
| JP | 09-318882 | 12/1997 |
| JP | 10-133307 | 5/1998 |
| JP | 10-145649 | 5/1998 |
| JP | 10-282428 | 10/1998 |
| JP | 2000-199857 | 7/2000 |
| JP | 2002-350736 | 12/2002 |
| JP | 2003-062003 | 3/2003 |
| JP | 2004-309930 | 11/2004 |

* cited by examiner

*Primary Examiner*—Alessandro Amari
(74) *Attorney, Agent, or Firm*—Kenyon & Kenyon LLP

(57) ABSTRACT

By adding perspective information in addition to binocular parallax, the invention provides a three-dimensional medical imaging apparatus that allows surgery to be performed with a more natural three-dimensional view, similar to that achieved with the naked eye. The three-dimensional medical imaging apparatus includes an image-acquisition optical system and an imaging device for acquiring three-dimensional images of a subject. The image-acquisition optical system includes an objective optical system for forming an image of the subject at an image-forming plane, and an entrance pupil position of the image-acquisition optical system is disposed between the objective optical system and the subject.

10 Claims, 12 Drawing Sheets

THREE-DIMENSIONAL MEDICAL IMAGING APPARATUS

This application is a divisional of U.S. patent application Ser. No. 11/288,339 filed on Nov. 29, 2005, now U.S. Pat. No. 7,453,631 which claims priority to Japanese Patent Application No. 2004-350265 filed on Dec. 2, 2004, each of which is expressly incorporated herein in its entirety by reference thereto.

BACKGROUND OF THE INVENTION

1. Field of the Invention

The present invention relates to a three-dimensional medical imaging apparatus used, for example, in surgical procedures, particularly in neurosurgery, ear, nose and throat surgery, orthopedic and plastic surgery, obstetric surgery, or ophthalmic surgery.

This application is based on Japanese Patent Application No. 2004-350265, the content of which is incorporated herein by reference.

2. Description of Related Art

In the related art, surgical microscopes are used to carry out magnified examination of minute operative sites in neurosurgery and so on. With organs formed of minute tissue, such as the brain, it is difficult to identify their tissue structure with the naked eye, and therefore, the treatment of these organs is normally carried out under a microscope. In neurosurgical procedures, which are carried out in very small regions on extremely critical and delicate tissue like blood vessels and nerves, not only is the tissue observed, but treatment such as joining and rerouting blood vessels and nerves, removing tumors, and the like is actually performed. Accordingly, it has become an important function of conventional surgical microscopes to allow the users to three dimensionally recognize an object to be examined in order to perform the treatment as well as allowing observation of a magnified image of the object to be examined.

Generally, humans obtain various kinds of information when observing a three-dimensional object with the eyes. This information includes binocular parallax, perspective (that is, distant objects are diminished and near objects are magnified), blurring in the depth direction, occlusion of objects, experience, knowledge, memory, and so forth. Here, it is assumed that an unknown specimen (an object that has never been seen before) is placed on a level platform and examined by illuminating it from all sides so that there are no shadows (conditions which are common in microscopy). In such a case, of the information for three-dimensionally capturing the object described above, occlusion, knowledge, experience, and so forth are not useful, but binocular parallax is effective in helping to determine the depth of the object. Surgical microscopes provide a three-dimensional view using binocular parallax to obtain depth information about the object under examination (for example, see Japanese Unexamined Patent Application Publication No. HEI-10-282428).

The surgical microscope disclosed in the above-cited Japanese Unexamined Patent Application Publication No. HEI-10-282428 includes two beams, one for the right eye and one for the left eye, and is configured such that the two beams pass through an eyepiece optical system and are observed. The operator sees the right and left images of the object under examination, which have parallax, with his or her right and left eyes, respectively, and these images are fused in the operator's brain, thus allowing a three-dimensional image of the object under examination to be observed.

Recently, instead of eyepiece optical systems, three-dimensional medical imaging apparatuses including imaging devices located near the image-forming planes in the left and right light paths have begun to be used. Three-dimensional medical observation apparatuses have also begun to be used which are configured such that three-dimensional observation of the object under examination is achieved by displaying images acquired by the three-dimensional medical imaging apparatus on a three-dimensional display device.

The field angles of a surgical microscope in the second embodiment disclosed in Japanese Unexamined Patent Application Publication No. HEI-10-282428 for various working distances (WD) and fields of view are shown in Table 1.

TABLE 1

| Objective focal length (mm) | Field of view (mm) | Field angle (tan θ) | Field angle (degree) |
|---|---|---|---|
| 335 | 29.1 | 0.025 | 1.461 |
| 385 | 35.2 | 0.039 | 2.232 |
| 465 | 44.9 | 0.054 | 3.107 |
| 335 | 14.5 | 0.002 | 0.124 |
| 385 | 17.6 | 0.011 | 0.614 |
| 465 | 22.4 | 0.020 | 1.161 |
| 335 | 7.2 | 0.031 | 1.749 |
| 385 | 8.8 | 0.030 | 1.705 |
| 465 | 11.2 | 0.029 | 1.676 |

As shown in Table 1, all field angle are extremely small (a few degrees). Surgical procedures using surgical microscopes generally involve treatment, not just examination, and therefore a surgical instrument or the like for performing treatment on the operative site is frequently moved in the observation field of view.

In such a case, if the field angle is narrow, there is no substantial change in the size of the observed image with depth, even if the surgical instrument is moved in the optical axis direction of the objective optical system. In other words, there is no perspective. Normally, when a person carries out observation with the naked eye, near objects are magnified and distance objects are diminished. Therefore, a sense of depth is obtained based on the degree of change in size of the object observed with the naked eye as the object moves.

This point is described in more detail in FIGS. 12A to 12C and FIGS. 13A to 13C.

FIGS. 12A to 12C illustrate the sense of depth when observing an object that moves in the direction of the line of vision of an observer when the field angle is small. FIGS. 13A to 13C show the sense of depth when observing an object that moves in the direction of the line of vision of an observer when the field angle is large. FIGS. 12A and 13A show the object approaching the observer, and FIGS. 12B, 12C, 13B, and 13C show the observation fields of view when the object approaches the observer.

Even though a sphere becomes closer to and further away from the observer in the same way, the view perceived by the observer when viewing the sphere differs depending on the different field angles.

More specifically, as shown in FIGS. 12A to 12C, when the field angle is narrow, it is difficult to obtain any perspective, and therefore, it is difficult to determine that the sphere is approaching the observer. This is because, even when the distance between the observer and the sphere changes, the size of the sphere as seen by the observer does not largely change.

In a wide observation field angle as shown in FIGS. 13A to 13C, the change in the size of the sphere as seen by the observer when the distance between the observer and the sphere changes is large, and therefore, perspective is easily obtained. Therefore, the observer can get a sense of perspective in the observation field of view. As a result, it is possible to obtain a sense of depth in the images displayed on a two-dimensional monitor that is not capable of displaying three-dimensionally because the contribution made by this perspective is substantial.

Since surgical microscopes generally obtain depth information about the object under examination based on binocular parallax, it is difficult to obtain perspective for an object moving within the observation field of view. Therefore, while perceiving an extremely unnatural sense of depth that is different from the sense of depth perceived when observing an object with the naked eye, such an effect must be continuously corrected for in the observer's brain while carrying out the surgical procedure, which causes the observer to become extremely fatigued.

Of course, a similar problem also exists even in three-dimensional medical imaging apparatuses in which the eyepiece optical system in the surgical microscope is replaced with an imaging device and in three-dimensional medical observation apparatuses for displaying an acquired image on a three-dimensional display device and observing it.

BRIEF SUMMARY OF THE INVENTION

The present invention has been conceived in order to overcome the problems described above, and an object thereof is to provide a three-dimensional medical imaging apparatus that allows surgery to be performed with a more natural three-dimensional view, similar to that achieved with the naked eye, by adding perspective (meaning that distant objects are diminished and near objects are magnified), in addition to binocular parallax.

In order to achieve the object described above, the present invention provides the following solutions.

According to a first aspect, the present invention provides a three-dimensional medical imaging apparatus for acquiring three-dimensional images of a subject, including an image-acquisition optical system; and an imaging device. The image-acquisition optical system includes an objective optical system for forming an image of the subject on an image-forming surface, and an entrance pupil position of the image-acquisition optical system is disposed between the objective optical system and the subject.

In the first aspect of the invention described above, the image-acquisition optical system preferably further includes a pair of variable-magnification optical systems, and within a range of magnifications that can be varied by the variable-magnification optical system, when at least one magnification is set, the entrance pupil position of the image-acquisition optical system is preferably located between the objective optical system and the subject.

In the first aspect of the invention described above, the image-acquisition optical system preferably further includes a variable-magnification optical system that adjusts the size of an image of the subject to be acquired by the imaging device; and within a range of magnifications that can be varied by the variable-magnification optical system, when the magnification is set to be in at least a low-magnification region, the entrance pupil position of the image-acquisition optical system is preferably located between the objective optical system and the subject.

In the first aspect of the invention described above, the image-acquisition optical system preferably further includes a variable-magnification optical system that adjusts the size of an image of the subject to be acquired by the imaging device; and within a range of magnifications that can be varied by the variable-magnification optical system, when the magnification is set so that the field of view on the surface of the subject is 40 mm or more in the in-focus region of the image-acquisition optical system, the entrance pupil position of the image-acquisition optical system is preferably located between the objective optical system and the subject.

In the first aspect of the invention described above, the field of view is preferably defined by an effective pixel area of the imaging device.

According to a second aspect, the present invention provides a three-dimensional medical imaging apparatus for acquiring three-dimensional images of a subject, comprising an image-acquisition optical system; and an imaging device. The image-acquisition optical system includes an objective optical system for forming an image of the subject at an image-forming plane and a relay optical system for conveying the image formed by the objective optical system to the vicinity of the image-acquisition surface of the imaging device; and the objective optical system is disposed between a pupil position set in the relay optical system and a conjugate position thereof.

In the second aspect of the invention described above, the relay optical system preferably includes a variable-magnification optical system for adjusting the size of an image of the subject to be acquired by the imaging device; and the variable-magnification optical system is disposed between the pupil position set inside the relay optical system and the imaging device.

In the second aspect of the invention described above, the relay optical system preferably includes a collimator optical system that takes an incident beam from the objective optical system side and emits the incident light beam as an afocal beam at the imaging device side, and an image-forming optical system that images the afocal beam emitted by the collimator optical system at the image-acquisition surface of the imaging device; the collimator optical system is preferably disposed between the objective optical system and the variable-magnification optical system; and the image-forming optical system is preferably disposed between the variable-magnification optical system and the imaging device.

In the second aspect of the invention described above, the relay optical system preferably includes a variable-magnification optical system for adjusting to a desired size the size of an image of the subject to be acquired by the imaging device and for taking a light beam incident from the objective optical system side and emitting the incident beam as an afocal light beam at the imaging device side, and an image-forming optical system for imaging the afocal light beam emitted by the variable-magnification optical system at an image-acquisition surface of the imaging device; the variable-magnification optical system is preferably disposed between the pupil position set inside the relay optical system and the imaging device; and the image-forming optical system is preferably disposed between the variable-magnification optical system and the imaging device.

According to a third aspect, the present invention provides a three-dimensional medical imaging apparatus for acquiring three-dimensional images of a subject, comprising: an image-acquisition optical system; and an imaging device. Conditional expressions (1) and (2) below are satisfied:

$$100 \leq WD \leq 500 \tag{1}$$

$$90 \leq 2\theta \leq 45° \tag{2}$$

where WD is the working distance of the three-dimensional medical imaging apparatus in millimeters and θ is the half field angle of the image-acquisition optical system.

In the third aspect of the invention described above, the image-acquisition optical system preferably includes an objective optical system for forming an image of the subject at an image-forming plane, and a variable-magnification optical system for adjusting the size of an image of the subject to be acquired by the imaging device; and within a range of magnifications that can be varied by the variable-magnification optical system, when at least one magnification is set, an entrance pupil position of the image-acquisition optical system is preferably disposed between the objective optical system and the subject.

According to a fourth aspect, the present invention provides a three-dimensional medical imaging apparatus for acquiring three-dimensional images of a subject, comprising an image-acquisition optical system; and an imaging device. The image acquisition optical system includes an objective optical system for forming an image of the subject at an image-forming plane, and a variable-magnification optical system for adjusting the size of an image of the subject to be acquired by the imaging device, and within a range of magnifications that can be varied by the variable-magnification optical system, when at least one magnification is set, conditional expressions (1) and (2) shown above are satisfied.

In the fourth aspect of the invention described above, the field of view on the surface of the subject in an in-focus region of the image-acquisition optical system preferably satisfies conditional expression (3) below:

$$5 \leq r \leq 200 \tag{3}$$

where r is the size in millimeters of the field of view of the image-acquisition optical system.

In the fourth aspect of the invention described above, the field of view is defined by the effective pixel area of the imaging device.

According to a fifth aspect, the present invention provides a three-dimensional medical imaging apparatus for acquiring three-dimensional images of a subject, comprising a pair of left and right imaging units, each imaging unit including an image-acquisition optical system and an imaging device. The central axes of the left and right image-acquisition optical systems are disposed in parallel, and the left and right imaging devices are decentered with respect to the central axes of the respective image-acquisition optical systems in directions such that the left and right imaging devices move away from each other.

In the fifth aspect of the invention described above, each image-acquisition optical system preferably includes an objective optical system for forming an image of the subject at an image-forming plane, and a variable-magnification optical system for adjusting the size of an image to be acquired by the imaging device; and within a range of magnifications that can be varied by the variable-magnification optical system, when at least one magnification is set, an entrance pupil position of the image-acquisition optical system is preferably disposed between the objective optical system and the subject.

The fifth aspect of the invention described above preferably further comprises a stop disposed in the vicinity of the pupil position set inside the relay optical system; and a moving mechanism for moving the stop in the optical axis direction of the relay optical system within a predetermined range including the pupil position.

The fifth aspect of the invention described above preferably further comprises a moving mechanism, wherein the relay optical system includes a variable-magnification optical system for adjusting the size of an image of the subject to be acquired by the imaging device, and the moving mechanism moves the stop to a predetermined position in association with the magnification-varying operation of the variable-magnification optical system.

For example, in optical systems having a relatively small observation field of view, such as surgical microscopes, a wide observation field angle can be ensured by disposing the entrance pupil position of the optical system close to the subject.

By disposing the entrance pupil position of the image-acquisition optical system forming the three-dimensional medical imaging apparatus between the subject and the surface at the most subject side of the image-acquisition optical system, the three-dimensional medical imaging apparatus of the present invention is configured such that an observation field of view of appropriate range is ensured and perspective information is added to the acquired image. The required observation field angle conditions for adding perspective information to the image acquired by the three-dimensional medical imaging apparatus and provided by the three-dimensional medical observation apparatus are shown below.

FIG. 11 shows the acquisition of an image of a subject (object plane) O by an image-acquisition unit including an image-acquisition optical system L and an imaging device C. The pupil position of the image-acquisition optical system L is indicated by P, half of the observation field angle is indicated by θ, and case where a subject of height r, which is within the depth of field of the image-acquisition unit, is imaged is considered. When the subject moves by distance d, as shown in FIG. 11, the height r' of the subject imaged by the image-acquisition unit is given by equation (4) below:

$$r' = d \times \tan\theta \tag{4}$$

Therefore, the relative change in the observation field of view of the image-acquisition unit is given by equation (5) below:

$$r/r' = r/(r - d \times \tan\theta) \tag{5}$$

In surgery using a surgical microscope, the region in which the surgeon moves a surgical instrument within the observation field of view of the surgical microscope is about ¼ of the observation field of view. Thus, replacing d=r/2 in equation (5), the optimum conditions for obtaining an image with perspective at the obtained relative change in the observation field of view of the three-dimensional medical observation apparatus are as defined in expression (6) below:

$$1.04 < 1/(1 - \tan\theta/2) < 1.27 \tag{6}$$

If the lower limit of expression (6) is not satisfied, the relative change in the size of the subject is small even though the subject moves within the observation field of view, and therefore, the three-dimensional medical imaging apparatus cannot add perspective information to the acquired image. Accordingly, the surgeon cannot experience a sense of depth from the observed image.

If the upper limit of expression (6) is not satisfied, the relative change in the size of the subject becomes excessively large when the subject is moved within the observation field of view, and conversely, the surgeon thus experiences some sense of disorientation or confusion when observing the three-dimensional image. This may cause the surgeon to become fatigued, which is not desirable. When determining θ from expression (6), $8.8° < 2\theta < 46°$, and therefore, the observation field angle conditions required for adding perspective information to the image acquired by the three-dimensional medical imaging apparatus and provided by the three-dimensional medical observation apparatus are as shown in expression (7) below:

$$9°<2\theta<45°  \quad (7)$$

The working distance WD (measured in millimeters) of the three-dimensional medical observation apparatus according to the present invention preferably satisfies expression (8) below:

$$100 \leq WD \leq 500 \quad (8)$$

If the lower limit in expression (8) is not satisfied, the working distance WD is too short, there is insufficient space for moving forceps or the like within the observation field of view, and the surgical procedure is thus made more difficult, which is undesirable. Also, by configuring the three-dimensional medical imaging apparatus of the present invention such that the optical axes of a pair of left and right image-acquisition optical systems intersect close to the surface of the subject, parallax is provided in the images acquired by the left and right image-acquisition devices. Therefore, if the working distance WD increases and does not satisfy the upper limit in expression (8), the size of the apparatus increases. This is undesirable since it reduces the ease of use of the apparatus.

The three-dimensional medical imaging apparatus according to the present invention may include a variable-magnification optical system, in the image-acquisition optical system, for adjusting the size of the acquired image. In such a case, by carrying out a magnification varying operation using the variable-magnification optical system, the field of view on the surface of the subject in the in-focus region of the image-acquisition optical system is preferably varied within the range shown in expression (9) below:

$$5 \leq r \leq 200 \quad (9)$$

where r is the size of the field of view in millimeters.

If the lower limit in expression (9) is not satisfied, object to be observed is magnified to completely fill the observation field of view, and since it no longer necessary to move the surgical instrument by a large amount within the observation field, it is not necessary to add perspective information to the three-dimensional image to experience a sense of depth. Also, if the upper limit in expression (9) is not satisfied, the proportion of the observation field of view occupied by the object to be observed is too small to be of any use.

According to the three-dimensional medical imaging apparatus of the present invention, disposing the entrance pupil position of the image-acquisition optical system between the subject and the most subject-side surface of the image-acquisition optical system provides an advantage in that surgery can be carried out with a more natural three-dimensional effect, close to that achieved with the naked eye, by adding perspective information, in addition to binocular parallax.

DETAILED DESCRIPTION OF THE INVENTION

First Embodiment

A first embodiment of the present invention will be described below with reference to FIGS. 1 to 3 and FIGS. 4A and 4B.

Figure 1:
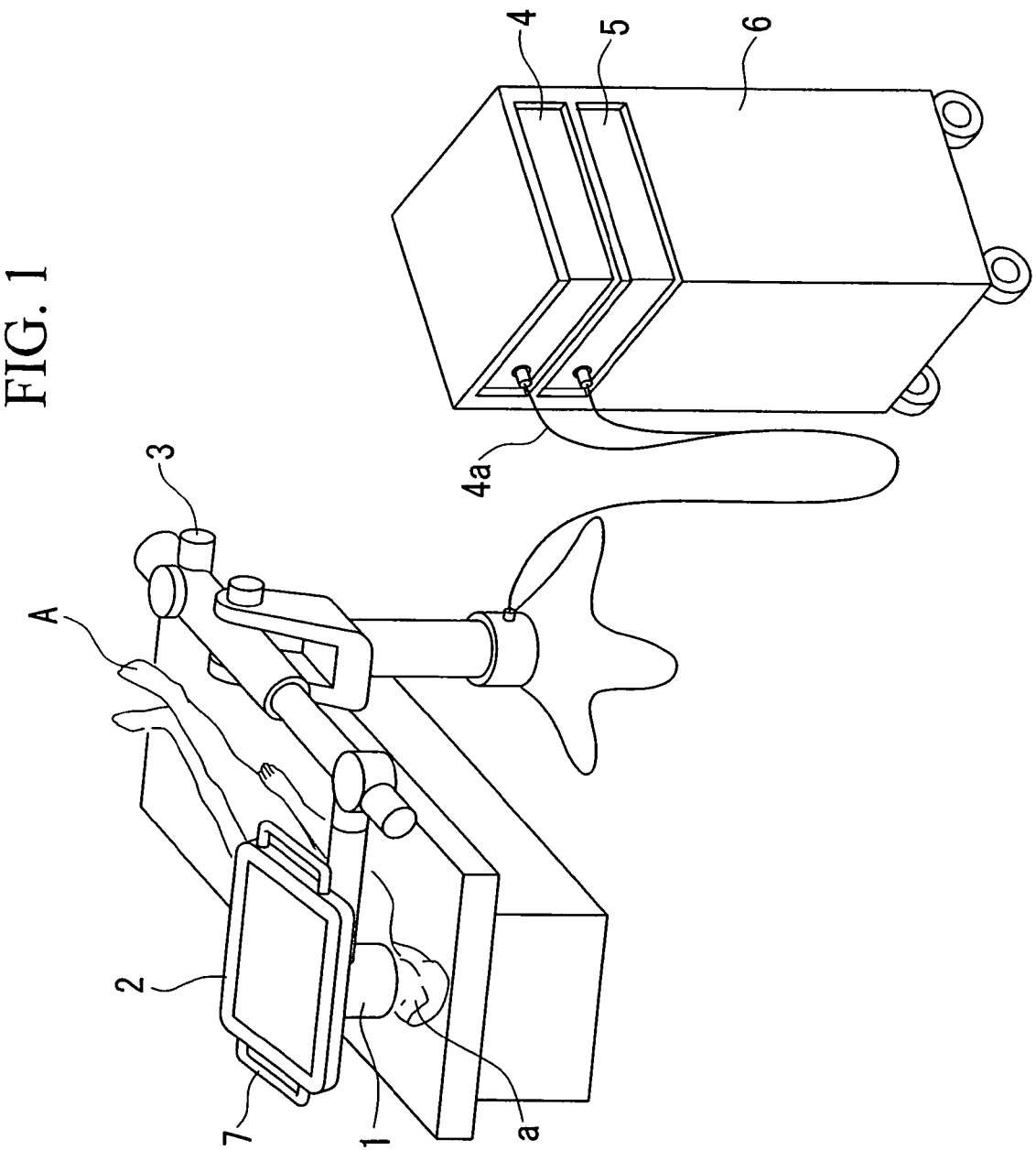
FIG. 1 is an overall system view including a three-dimensional medical imaging apparatus according to a first embodiment of the present invention.
Figure 2:
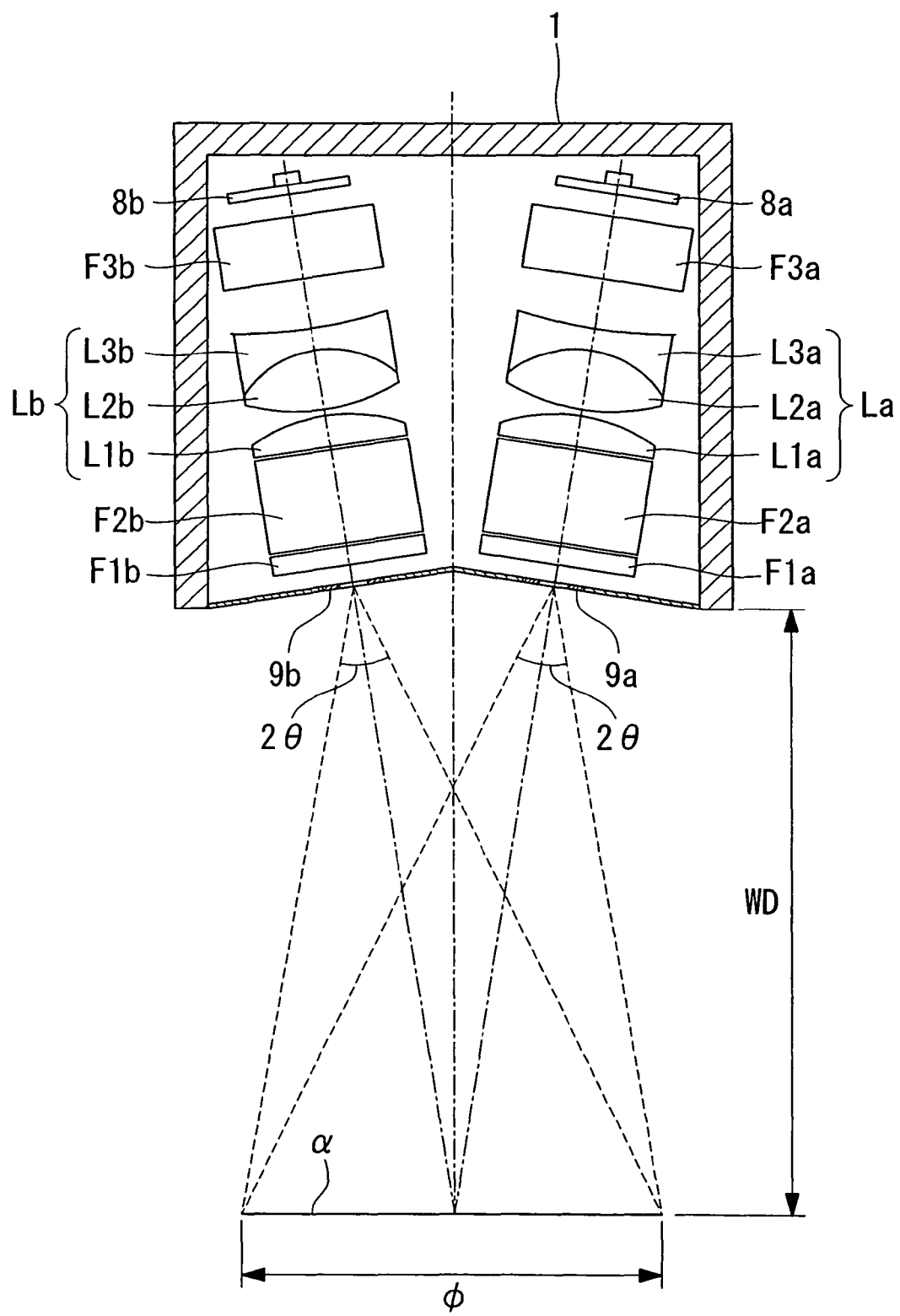
FIG. 2 is a diagram showing the configuration of an image-acquisition optical system in the three-dimensional medical imaging apparatus in FIG. 1.
Figure 3:
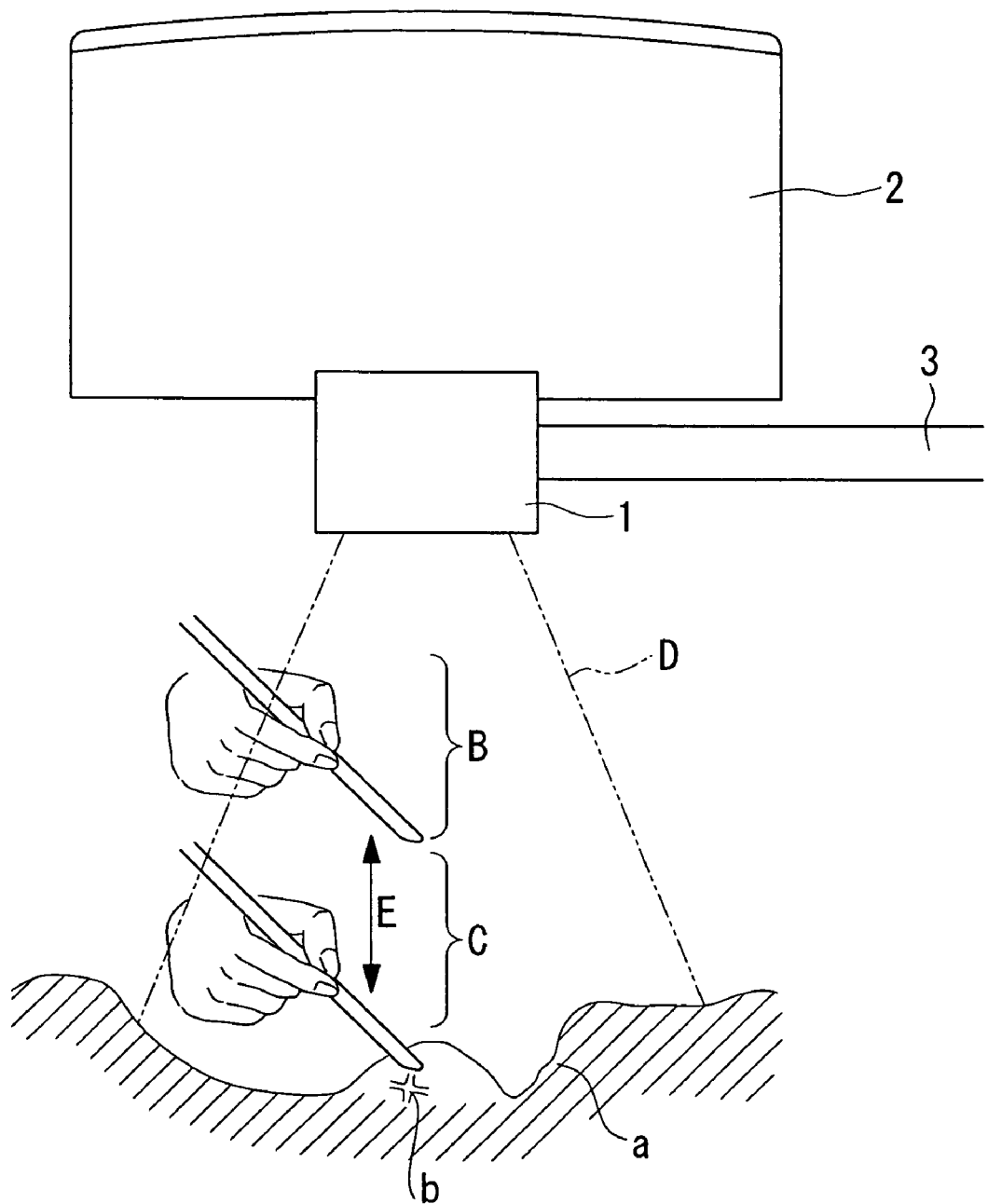
FIG. 3 is a diagram showing the movement of a surgical instrument with respect to an operative site in a surgical procedure using the three-dimensional medical imaging apparatus in FIG. 1.
Figure 4A:
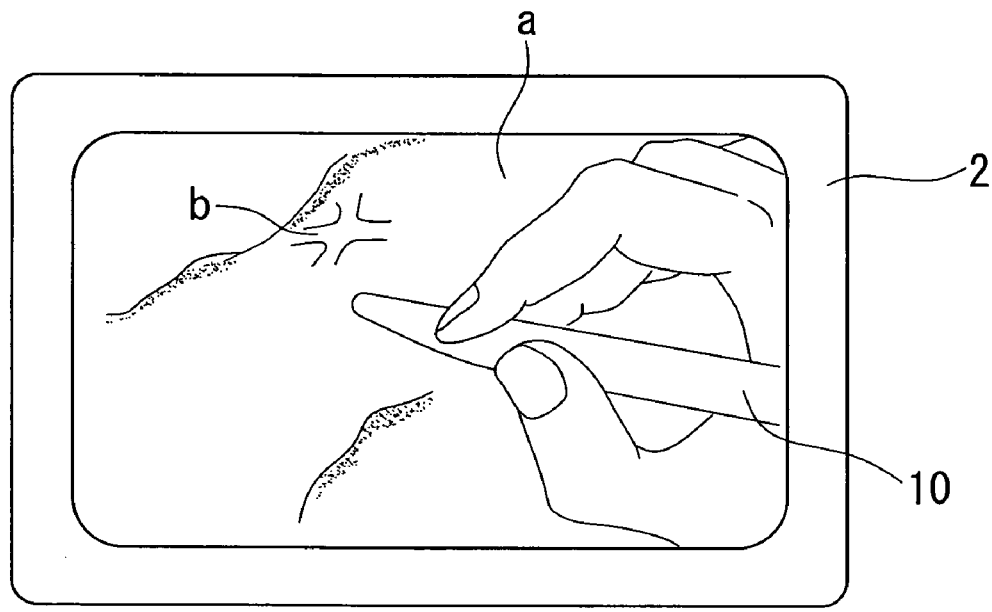
FIGS. 4A and 4B are diagrams showing the operative area displayed on a display device in FIG. 1 when moving the surgical instrument.
Figure 4B:
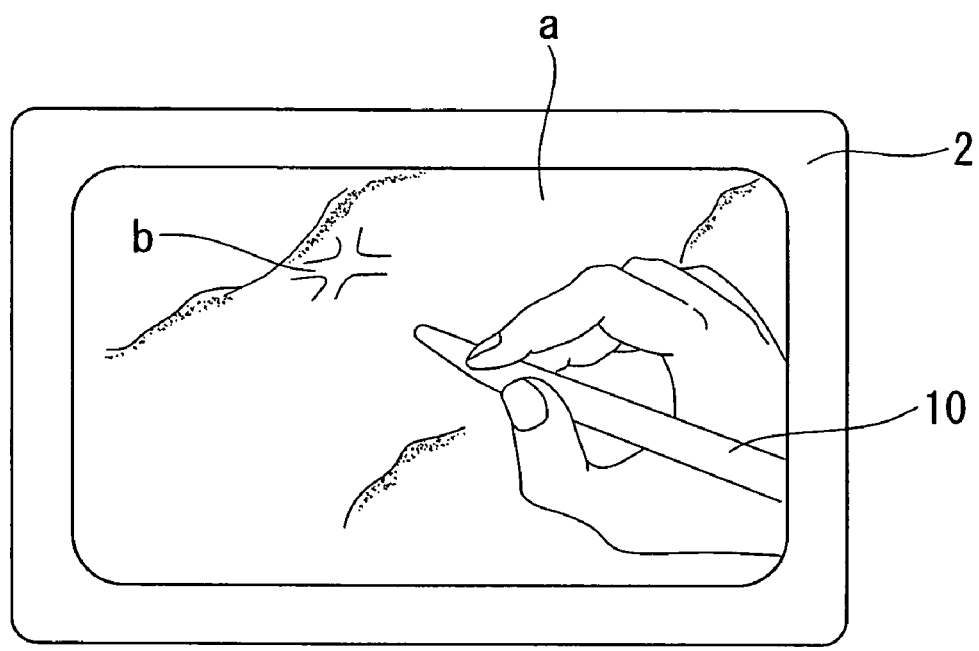

FIG. 1 is an overall view of the system, including a three-dimensional medical imaging apparatus according to this embodiment, FIG. 2 is a view showing the configuration of an image-acquisition optical system in the three-dimensional medical imaging apparatus according to this embodiment, FIG. 3 is a diagram illustrating the motion of a surgical instrument with respect to an operative site in a surgical procedure using the three-dimensional medical imaging apparatus, and FIGS. 4A and 4B are diagrams illustrating the operative area displayed on a display device when moving the surgical instrument.

The configuration of the overall system according to this embodiment will now be described with reference to FIG. 1.

In FIG. 1, reference numeral 1 indicates a three-dimensional medical imaging apparatus for examining an operative site a, which is a subject α, to carry out a surgical procedure on a patient A; and reference numeral 2 indicates a 3D monitor that can three-dimensionally display the examination site acquired with the three-dimensional medical imaging apparatus 1. The 3D monitor 2 is provided with grips 7. The three-dimensional medical imaging apparatus 1 and the 3D monitor 2 are connected to an arm 3 so that they can be moved to a position allowing easy examination of the operative site a and fixed at that position. Reference numeral 4 indicates a light source. Light emitted from the light source 4 is conveyed to the operative site a via a light guide 4a that passes through the arm 3 and is connected to the three-dimensional medical imaging apparatus 1. Reference numeral 5 indicates a camera control unit (hereinafter referred to as CCU) which is connected to the three-dimensional medical imaging apparatus 1 and the 3D monitor 2 via the arm 3, converts the image-acquisition signal from the three-dimensional medical imaging apparatus 1 into a picture signal, and transmits it to the 3D monitor 2. The light source 4 and the CCU 5 are housed in a trolley 6.

The configuration of the image-acquisition optical system of the three-dimensional medical imaging apparatus 1 will now be described with reference to FIG. 2.

A right-eye objective optical system (objective optical system) La is constructed of three lenses L1a, L2a, and L3a, and a left-eye objective optical system (objective optical system) Lb is constructed of three lenses L1b, L2b, and L3b. F1a, F2a, F3a, F1b, F2b, and F3b are optical filters for cutting infrared light, eliminating Moire fringing, and so on. A right-eye CCD (imaging device) 8a captures images of the examination site from the right-eye objective optical system La, and a left-eye CCD (imaging device) 8b captures images of the examination site from the left-eye objective optical system Lb; the CCDs 8a and 8b then output the images to the CCU 5. Reference numeral 9a indicates a right-eye aperture stop (stop), and reference numeral 9b indicates a left-eye aperture stop (stop). The stops 9a and 9b are positioned at the operative site side of the respective objective optical systems and define the entrance pupil positions.

The field angles 2θ of the three-dimensional medical imaging apparatus are defined at the origins of the pupil positions, as shown in the figure. A working distance WD provided for the operator is defined as the distance from the lower surface of the three-dimensional medical imaging apparatus 1 to the subject α.

If the field angle is fixed, as above, as the working distance WD increases, the field of view Φ increases (low magnification), and as the working distance WD decreases, the field of view Φ decreases (high magnification). Also, the field of view on the picture displayed on the monitor screen is determined by the relationship between the effective pixel area of the image-acquisition surface of the imaging device and the size of the field of view Φ acquired at the image plane of the imaging device. For example, when the effective pixel area of the image-acquisition surface of the imaging device is rectangular and the field of view Φ acquired at the image-acquisition plane of the imaging device is large enough to be inscribed in the effective pixel area, what is actually displayed on the screen is a rectangular portion inscribed in the field of view Φ, and the diagonal of the rectangle corresponds to the diameter of the field of view Φ. The three-dimensional medical imaging apparatus 1 is a so-called Greenough-type observation system. Detailed lens data for the objective optical systems according to this embodiment is shown in Tables 2 and 3 below.

TABLE 2

| S | RDY | THI | Nd | Vd | Outer diameter |
|---|-----|-----|-----|-----|----------------|
| Obj | INF | 300 | | | |
| Stop-position | INF | 0.36 | | | 0.6 |
| 2 | INF | 0.4 | 1.51633 | 64.14 | 3 |
| 3 | INF | 0.03 | | | 3 |
| 4 | INF | 2 | 1.52287 | 59.89 | 3 |
| 5 | INF | 0.03 | | | 3 |

TABLE 2-continued

| S | RDY | THI | Nd | Vd | Outer diameter |
|---|-----|-----|-----|-----|----------------|
| 6 | INF | 0.6 | 1.6228 | 57.06 | 3 |
| 7 | −3.217 | 0.2 | | | 3 |
| 8 | 3.542 | 1.2 | 1.65844 | 50.88 | 3 |
| 9 | −1.904 | 0.47 | 1.78472 | 25.68 | 3 |
| 10 | 9.403 | 0.98 | | | 3 |
| 11 | INF | 1.31 | 1.51633 | 64.14 | 3 |
| 12 | INF | 0.4 | | | 3 |

TABLE 3

| Entrance pupil position | WD | Field angle (2W) | Field of view | Image height | Magnification |
|---|---|---|---|---|---|
| 0 | 300 | 35.8° | 183.7 | 2.264 | 0.012 |

Next, the operation of the three-dimensional medical imaging apparatus 1 according to the present embodiment, configured as described above, will be described.

As shown in FIG. 1, while holding the grips 7 and moving the arm 3, the surgeon places the three-dimensional medical imaging apparatus 1 and the 3D monitor 2 at a position where the operative site a can be examined.

Next, the surgeon carries out examination of the operative site a. Light irradiated from the light source 4 passes through the light guide 4a and illuminates the operative site a. Reflected light from the operative site a passes through the right-eye aperture stop 9a and the left-eye aperture stop 9b, the filters F1a, F2a, F1b, and F2b, the right-eye objective optical system La and the left-eye objective optical system Lb, and the filters F3a and F3b, and the right-eye light beam is imaged on the CCD 8a and the left-eye light beam is imaged on the CCD 8b. The right-eye CCD 8a and the left-eye CCD 8b respectively output right-eye and left-eye picture information to the CCU 5. The CCU 5 then outputs the received picture information on the 3D monitor 2, and the 3D monitor 2 displays the operative site a in three-dimensional form. The surgeon thus carried out three-dimensional examination of the operative site a by viewing the 3D monitor 2. Focus adjustment of the operative site a is carried out by holding the grips 7 and changing the distance between the operative site a and the three-dimensional medical imaging apparatus 1 using the arm 3.

Subsequently, the surgeon proceeds with the treatment. The operation of the system during treatment is described with reference to FIG. 3 and FIGS. 4A and 4B. When the surgeon identifies an affected area b in the operative site a, he or she grips the surgical instrument 10 (for example, forceps, an electric scalpel, or the like) and moves it to position B within the field of view of the three-dimensional medical imaging apparatus 1. More specifically, the surgeon places his or her hand inside a boundary D of the field of view, which is determined by the field angle 2θ of the three-dimensional medical imaging apparatus 1. At this point, the surgical instrument 10 is displayed on the 3D monitor 2, as shown in FIG. 4A.

Next, the surgeon moves the surgical instrument 10 towards the affected area b, that is, to position C shown in FIG. 3. At this point, the surgical instrument 10 is still displayed on the 3D monitor 2, as shown in FIG. 4B. In the present embodiment, since the entrance pupil positions of the optical systems provided in the three-dimensional medical imaging apparatus 1 are located further towards the front (the object side) than the object side surface of the right-eye objective optical systems La and left-eye objective optical system Lb, the field angle can be set wider than the case where the entrance pupils are located inside the objective optical systems. In an in-focus region of the objective optical systems, for movement of an object in the direction of arrow E in FIG. 3, the object appears larger the closer it is to the three-dimensional medical imaging apparatus 1, and it appears smaller the further away it is, as shown in FIGS. 4A and 4B.

A more natural stereoscopic effect can thus be obtained with the present embodiment. This is achieved because the system is configured as a Greenough-type optical system so that a human operator can easily obtain binocular-parallax information, similar to the conditions that occur when observing with the naked eye, and because the entrance pupils are located between the subject and the objective optical systems to set a wide field angle in order to give perspective information.

Although the three-dimensional medical imaging apparatus 1 and the 3D monitor 2 are integrated in the present embodiment, they may be independently supported by separate arms.

Second Embodiment

A second embodiment of the present invention will now be described with reference to FIG. 5. Parts having the same names and reference numerals as those in the first embodiment are identical to those in the first embodiment, and a description thereof shall be omitted here.

Figure 5:
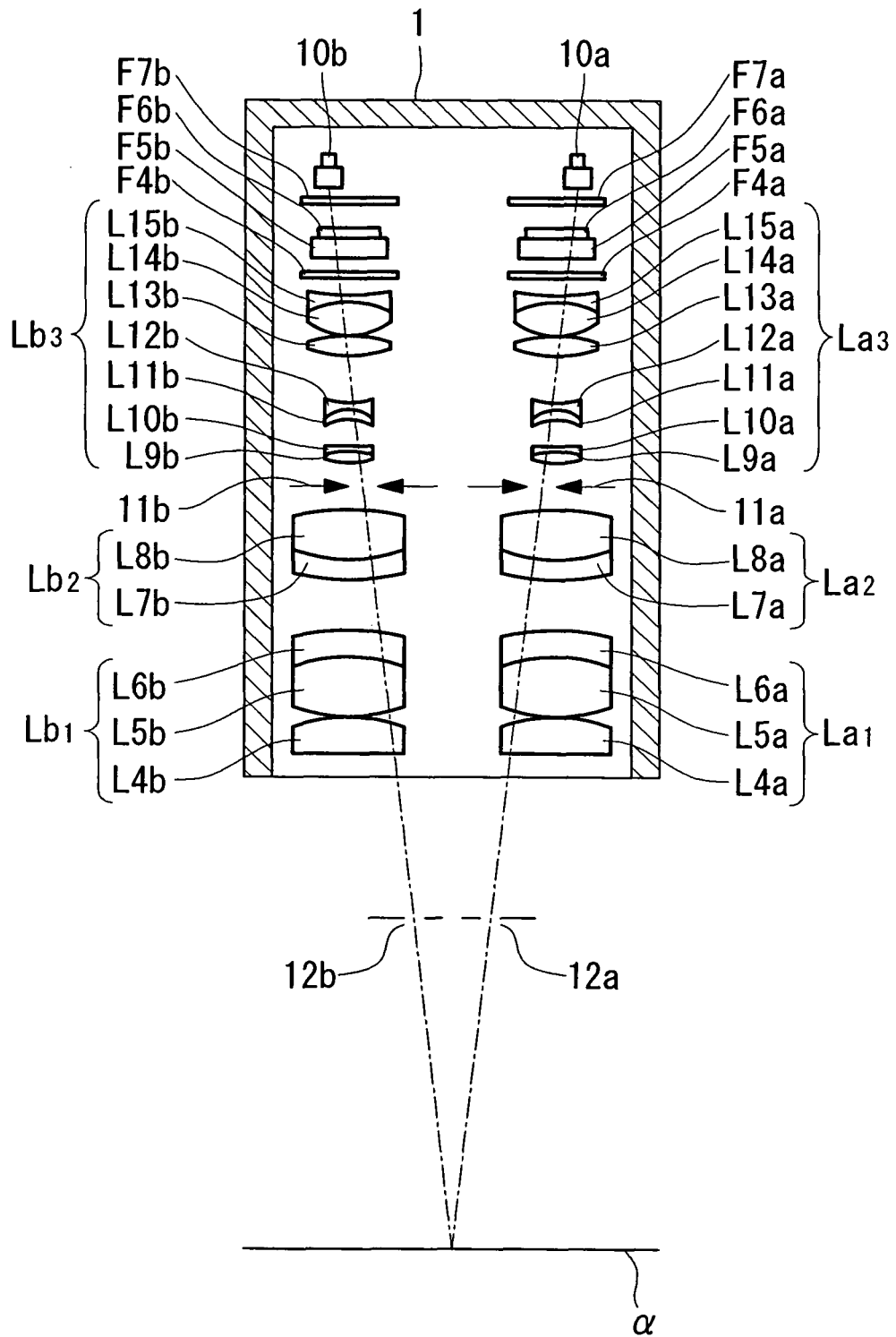
FIG. 5 is a diagram showing the configuration of an image-acquisition optical system in a three-dimensional medical imaging apparatus according to a second embodiment of the present invention.

FIG. 5 is a diagram showing the configuration of an image-acquisition optical system in the three-dimensional medical imaging apparatus 1 according to the present embodiment.

A right-eye objective optical system (objective optical system) La1 is constructed of three lenses L4a, L5a, and L6a, a right-eye collimator lens (collimator optical system) La2 is constructed of two lenses L7a and L8a, and a right-eye variable-magnification optical system (variable-magnification optical system) La3 is constructed of seven lenses L9a to L15a. Likewise, a left-eye objective optical system (objective optical system) Lb1 is constructed of three lenses L4b, L5b, and L6b, a left-eye collimator lens (collimator optical system) Lb2 is constructed of two lenses L7b and L8b, and a left-eye variable-magnification optical system (variable-magnification optical system) Lb3 is constructed of seven lenses L9b to L15b. F4a to F7a and F4b to F7b are optical filters for cutting infrared light, eliminating Moire fringing, and so on. A right-eye CCD 10a acquires an image of the object under examination from the right-eye variable-magnification optical system La3, and a left-eye CCD 10b acquires an image of the object under examination from the left-eye variable-magnification optical system Lb3. The CCDs 10a and 10b then output the acquired images to the CCU 5.

At this point, the right-eye CCD (imaging device) 10a and the left-eye CCD (imaging device) 10b are disposed towards the outer sides (in the figure, in directions such that the CCDs move away from each other) so as to be decentered from the centers of the effective pixel areas of the CCDs with respect to the optical axes of the optical systems La1 to La3 and Lb1 to Lb3, which are arranged in parallel. Accordingly, the left and right examination centers are coincident at the subject α.

Reference numeral 11a indicates a pupil position of the right-eye optical system in the three-dimensional medical imaging apparatus 1. The pupil position 11a of the right-eye optical system is relayed by the right-eye objective optical system La1 and the right-eye collimator lens La2 to a pupil position 12a, which is conjugate with the pupil position 11a of the right-eye optical system. Likewise, reference numeral 11b indicates a pupil position of the left-eye optical system in the three-dimensional medical imaging apparatus 1. The pupil position 11b of the left-eye optical system is relayed by the left-eye objective optical system Lb1 and the left-eye collimator lens Lb2 to a pupil position 12b which is conjugate with the pupil position 11b of the left-eye optical system.

With such a configuration, it is possible to obtain an effect equivalent to placing the entrance pupils of the left-eye and right-eye optical systems between subject a and the most object-side surface of the optical systems. Detailed lens data of the optical systems used in this embodiment is shown in Tables 4 to 6 below.

TABLE 4

| S | RDY | THI | Nd | Vd | Outer diameter |
|---|---|---|---|---|---|
| Obj | INF | 274.63 | | | |
| 1 | INF | 5.6 | 1.6968 | 55.53 | 16 |
| 2 | −23.5185 | 0.2 | | | 16 |
| 3 | 36.5688 | 8.6 | 1.51633 | 64.15 | 16 |
| 4 | −20.2031 | 3.6 | 1.80518 | 25.43 | 16 |
| 5 | −76.8737 | 63.32 | | | 16 |
| 6 | 59.952 | 2.54 | 1.78472 | 25.68 | 16 |
| 7 | 23.0932 | 7.34 | 1.66672 | 48.32 | 16 |
| 8 | −53.096 | 0.4 | | | 16 |
| 9 | INF | 30 | | | |
| Stop-position | INF | −4.9754 | | | 3 |
| 11 | INF | 0.2 | | | |
| 12 | INF | 9 | 1.51633 | 64.15 | 6.2 |
| 13 | INF | 3 | | | 6.2 |
| 14 | 13.718 | 1.37 | 1.71999 | 50.25 | 6.2 |
| 15 | −13.718 | 1 | 1.78472 | 25.71 | 6.2 |
| 16 | INF | d1 | | | 6.2 |
| 17 | −7.353 | 1.8 | 1.84666 | 23.78 | 4.5 |
| 18 | −3.718 | 1 | 1.6393 | 44.88 | 4.5 |
| 19 | 8.719 | d2 | | | 4.5 |
| 20 | 20.826 | 3 | 1.72916 | 54.68 | 11 |
| 21 | −16.575 | 0.3 | | | 11 |
| 22 | 10.433 | 4.8 | 1.51633 | 64.15 | 11 |
| 23 | −10.433 | 0.8 | 1.84666 | 23.78 | 11 |
| 24 | 82.282 | d3 | | | 11 |
| 25 | INF | 1 | 1.51633 | 64.15 | 11 |
| 26 | INF | 2 | | | 11 |
| 27 | INF | 3.08 | 1.54814 | 45.78 | 11 |
| 28 | INF | 0.05 | | | 11 |
| 29 | INF | 1.6 | 1.514 | 74 | 11 |
| 30 | INF | 3.67 | | | 11 |
| 31 | INF | 0.75 | 1.51633 | 64.15 | 11 |
| 32 | INF | 1.19 | | | 11 |
| 33 | INF | d4 | | | 11 |

TABLE 5

| | T | S | W |
|---|---|---|---|
| d1 | 3.64131 | 5.30217 | 6.28877 |
| d2 | 7.22513 | 3.70502 | 1.19364 |
| d3 | 2.30781 | 4.16705 | 5.69183 |
| d4 | 0.1221 | 0.10647 | 0.135 |

TABLE 6

| | Pupil position | WD | Field angle (2W) | Field of view | Image height | Magnification |
|---|---|---|---|---|---|---|
| T | −25 | 275 | 14° | 61 | 3.844 | 0.0631 |
| S | −25 | 275 | 19° | 82 | 3.844 | 0.047 |
| W | −25 | 275 | 28.4° | 126 | 3.844 | 0.031 |

Next, the operation of the three-dimensional medical imaging apparatus 1 according to this embodiment, having the above configuration, will be described.

In the same way as in the first embodiment, the operator first places the three-dimensional medical imaging apparatus 1 and the 3D monitor 2 at a position allowing observation of the operative site a, and he or she then carries out examination of the operative site a. Light irradiated from the light source 4 passes through the light guide 4a and illuminates the operative site a. Reflected light from the operative site a passes through the right-eye objective optical system La1 (the left-eye objective optical system Lb1), the right-eye collimator lens La2 (the left-eye collimator lens Lb2), the right-eye variable-magnification optical system La3 (the left-eye variable-magnification optical system Lb3), and the filters F4a to F7a (the filters F4b to F7b), and the right-eye light beam is imaged onto the right-eye CCD 10a (the left-eye light beam is imaged onto the left-eye CCD 10b). The right-eye CCD 10a and the left-eye CCD 10b respectively output right-eye and left-eye picture information to the CCU 5. Based on this picture information, the surgeon can carry out three-dimensional examination using the 3D monitor 2.

Next, the surgeon carries out treatment. Since the operation of the system at this point is the same as that in the first embodiment, a description thereof is omitted. While the surgeon is carrying out the treatment, by pushing a magnification-varying switch (not shown), the surgeon can shift a lens position-moving frame (not shown) with a motor or the like to change the positions of lenses L11a and L12a (L11b and L12b) in the variable-magnification optical system La3 (Lb3), which magnifies or reduces the picture of the operative site displayed on the monitor.

By constructing the optical systems in the way described above, while magnifying or reducing the operative site, the entrance pupil position 12a(12b) does not change and is always located between the objective lenses and the subject. Therefore, compared to the optical system employed in conventional surgical microscopes, a wide field angle can always be maintained for the same field of view.

Third Embodiment

A third embodiment of the present invention will now be described with reference to FIG. 6. Parts with the same names and same reference numerals as those in the first embodiment are identical to those in the first embodiment, and a description thereof shall thus be omitted here.

Figure 6:
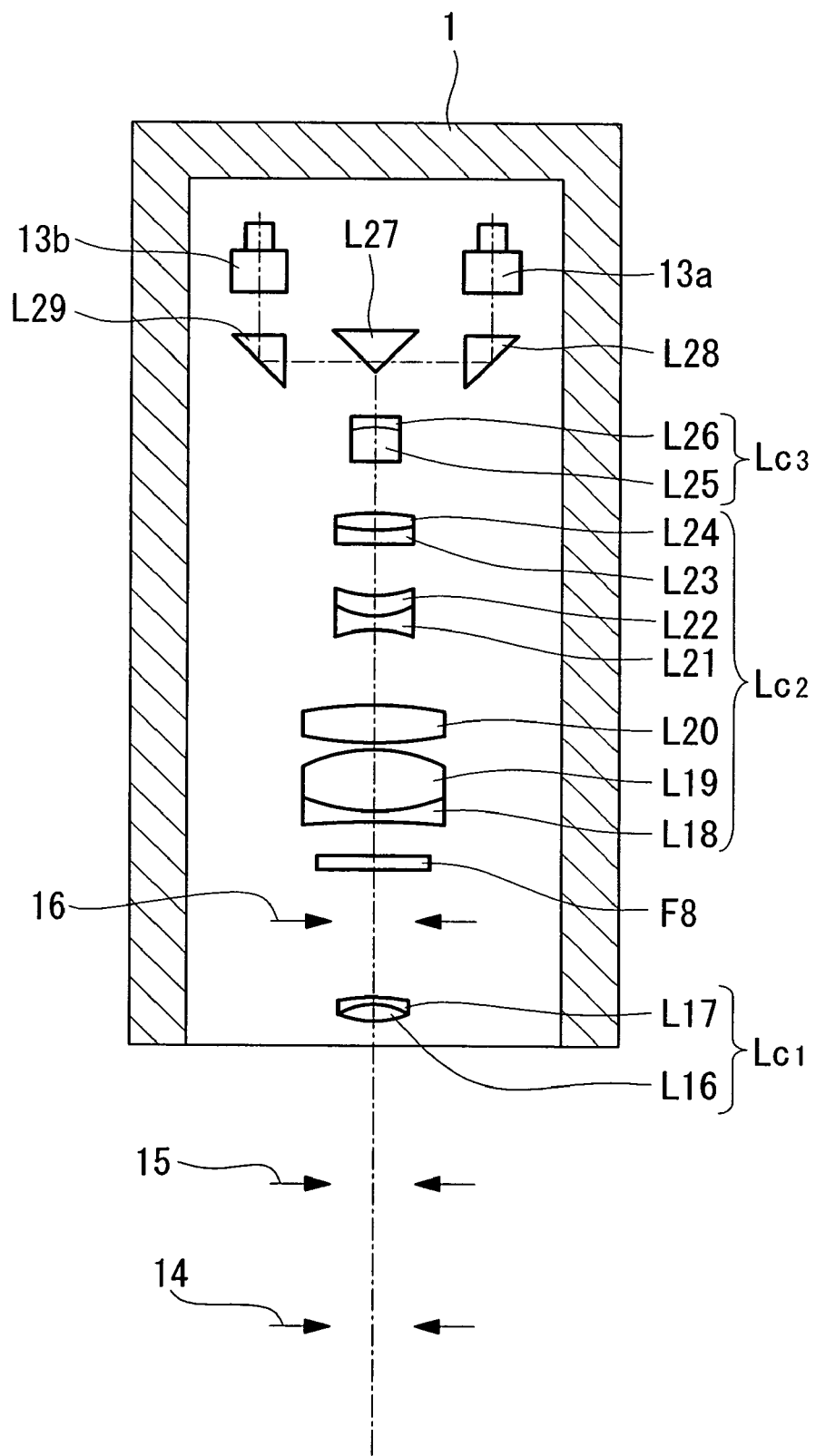
FIG. 6 is a diagram showing the configuration of an image-acquisition optical system in a three-dimensional medical imaging apparatus according to a third embodiment of the present invention.

FIG. 6 is a diagram showing the configuration of an image-acquisition optical system in the three-dimensional medical imaging apparatus according to this embodiment.

An objective optical system Lc1 is constructed of two lenses L16 and L17, a variable-magnification optical system Lc2 is constructed of seven lenses L18 to L24, and an image-forming optical system Lc3 is formed of two lenses L25 and L26. Reference numeral L27 is a pupil-division prism, and reference numerals L28 and L29 are reflection prisms. A right-eye CCD (imaging device) 13a acquires an image of the object under examination from the reflection prism L28, and a left-eye CCD (imaging device) 13b acquires an image of the object under examination from the reflection prism L29. F8 is an optical filter for cutting infrared light, eliminating Moire fringing, and so on. Reference numeral 14 indicates a pupil position used when the magnification is low, reference numeral 15 indicates a pupil position used when the magnification is intermediate, and reference numeral 16 indicates a pupil position used when the magnification is high. Detailed lens data of the optical systems used in the present embodiment is shown in Tables 7 to 9 below.

TABLE 7

| S | RDY | THI | Nd | Vd | Outer diameter |
|---|---|---|---|---|---|
| Obj | | 200 | | | |
| 1 | 9.3449 | 1.29 | 1.66672 | 48.32 | 5 |
| 2 | −4.0644 | 0.45 | 1.78472 | 25.68 | 5 |
| 3 | −10.5515 | 19.18 | | | 5 |
| 4 | INF | 1 | 1.51633 | 64.15 | 8 |
| 5 | INF | d1 | | | |
| 6 | −82.282 | 0.8 | 1.84666 | 23.78 | 10 |
| 7 | 10.433 | 4.8 | 1.51633 | 64.15 | 10 |
| 8 | −10.433 | 0.3 | | | 10 |
| 9 | 16.575 | 3 | 1.72916 | 54.68 | 10 |
| 10 | −20.826 | d2 | | | 10 |
| 11 | −8.719 | 1 | 1.6393 | 44.88 | 5 |
| 12 | 3.718 | 1.8 | 1.84666 | 23.78 | 5 |
| 13 | 7.353 | d3 | | | 5 |
| 14 | INF | 1 | 1.78472 | 25.71 | 6.2 |
| 15 | 13.718 | 1.37 | 1.71999 | 50.25 | 6.2 |
| 16 | −13.718 | 13.82 | | | 6.2 |
| 17 | 20.3889 | 2.82 | 1.66672 | 48.32 | 4 |
| 18 | −8.8678 | 0.98 | 1.78472 | 25.68 | 4 |
| 19 | −23.0216 | 4 | | | 4 |
| Stop-position | INF | 10 | | | 1.34 |
| 21 | INF | d4 | | | |

TABLE 8

| | T | S | W |
|---|---|---|---|
| d1 | 2.308 | 4.167 | 5.692 |
| d2 | 7.225 | 3.705 | 1.194 |
| d3 | 3.641 | 5.302 | 6.289 |
| d4 | 3.592 | 3.552 | 3.557 |

TABLE 9

| | Pupil position | WD | Field angle (2W) | Field of view | Image height | Magnification |
|---|---|---|---|---|---|---|
| T | 0.1 | 200 | 11° | 39 | 2.2 | 0.046 |
| S | −6.4 | 200 | 17° | 60 | 2.2 | 0.031 |
| W | −8.7 | 200 | 24° | 83 | 2.2 | 0.023 |

Next, the operation of the three-dimensional medical imaging apparatus 1 according to the present embodiment, having the above configuration, will be described.

In the same way as in the first embodiment, the surgeon places the three-dimensional medical imaging apparatus and the 3D monitor 2 at a position allowing the operative site a to be observed and then carries out examination of the operative site a at low magnification, which allows the entire operative site a to be observed. In the present invention, in order to observe the entire operative site when the field of view Φ is 50 mm or above, the magnification is set to be low.

Illumination light irradiated from the light source 4 passes through the light guide 4a and irradiates the operative site a. Reflected light from the operative site a passes through the objective optical system Lc1, the filter F8, the variable-magnification optical system Lc2, and the image-forming optical system Lc3 in the image-acquisition optical system, and the pupil-division prism L27 disposed at the pupil position splits the pupil into a right-eye light beam and a left-eye light beam. The right-eye light beam is deflected by the reflection prism L28 and is acquired by the right-eye CCD 13a, and the left-eye light beam is deflected by the reflection prism L29 and is acquired by the left-eye CCD 13*b*. The right-eye CCD 13*a* and the left-eye CCD 13*b* respectively output right-eye and left-eye picture information to the CCU 5. Based on this picture information, the surgeon can carry out three-dimensional examination using the 3D monitor 2.

Since three-dimensional observation is carried out with pupil division using the single variable-magnification optical system Lc2, the three-dimensional medical imaging apparatus can be reduced in size.

Next, the surgeon carries out the treatment. Since the operation of the system here is the same as in the first embodiment, a description thereof is omitted. While the surgeon is carrying out the treatment, by pushing a magnification-varying switch (not shown), the surgeon can shift a lens position-moving frame (not shown) by controlling a motor (not shown) or the like to change the positions of lenses L22 and L21 in the variable-magnification optical system Lc2, thus magnifying the operative site. While magnifying the operative site, the entrance pupil position of the image-acquisition optical system moves away from the operative site as the magnification increases (it moves to position 14 when the magnification is low, to position 15 when the magnification is intermediate, and to position 16 when the magnification is high). Accordingly, as the magnification increases, the entrance pupil moves closer to the entrance pupil poison of the conventional surgical microscope, and the perspective (meaning that distant objects are diminished and near objects are magnified) is thus reduced. The present embodiment is configured such that, within the range of magnifications that can be varied by the variable-magnification optical system Lc2, at a magnification (from low to intermediate magnification) where the field of view on the subject surface (the operative site) is 40 mm or above in the in-focus region of the image-acquisition optical system, the entrance pupil position of the image-acquisition optical system is disposed between the objective optical system Lc1 and the subject (operative site).

Since three-dimensional observation can be carried out with pupil division using the single variable-magnification optical system Lc2, the apparatus can be reduced in size.

In general, when performing treatment deep inside a hole or the like while observing at high magnification, if the perspective is strong, it may be difficult to carry out an extremely delicate operation because the part to be examined appears small even though the magnification is high. Conversely, the stronger depth effect at low magnification is closer to that achieved with the naked eye, which allows the surgical procedure to be carried out while providing a more natural view. Therefore, in the present embodiment, by making the entrance pupil approach the subject as the magnification goes from intermediate to low, the perspective effect becomes stronger, and by pulling the entrance pupil away from the subject at high magnification, the perspective becomes weaker. The perspective effect is thus changed such that the surgical procedure can be easily performed.

Fourth Embodiment

A fourth embodiment of the present invention will now be described with reference to FIG. 7. Parts having the same names and the same reference numerals as those in the first embodiment are identical to those in the first embodiment, and a description thereof shall be omitted here.

Figure 7:
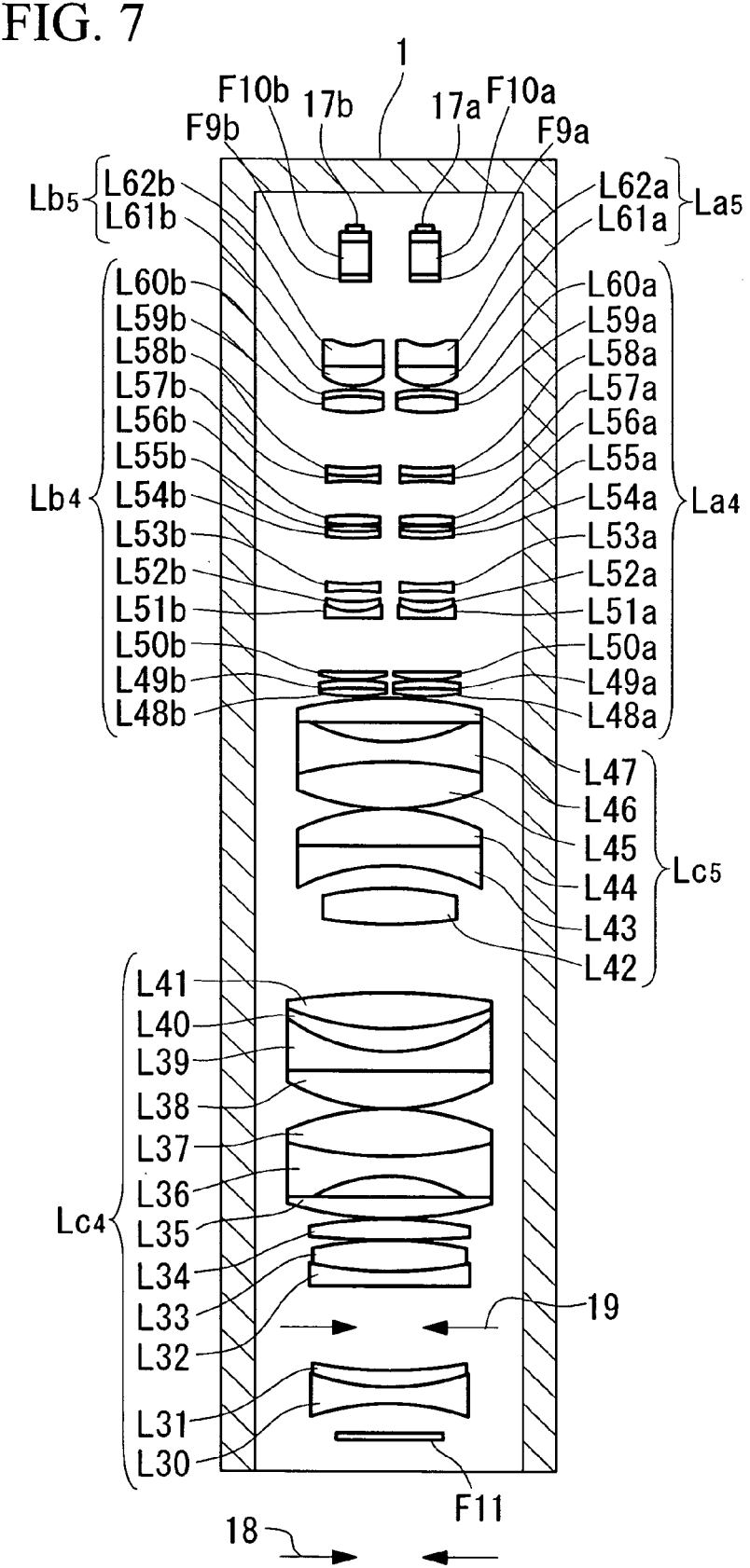
FIG. 7 is a diagram showing the configuration of an image-acquisition optical system in a three-dimensional medical imaging apparatus according to a fourth embodiment of the present invention.

FIG. 7 is a diagram showing the configuration of an image-acquisition optical system in a three-dimensional medical imaging apparatus according to the present embodiment.

A variable-focal-length objective optical system Lc4 is constructed of eleven lenses L30 to L41, a collimator lens (collimator optical system) Lc5 is constructed of six lenses L42 to L47, a right-eye variable-magnification optical system (variable-magnification optical system) La4 is constructed of thirteen lenses L48*a* to L60*a*, and a left-eye variable-magnification optical system (variable-magnification optical system) Lb4 is constructed of thirteen lenses L48*b* to L60*b*. Also, a right-eye image-forming optical system (image-forming optical system) La5 is constructed of two lenses L61*a* and L62*a*, and a left-eye image-forming optical system (image-forming optical system) Lb5 is constructed of two lenses L61*b* and L62*b*. F9*a*, F10*a*, F9*b*, F10*b*, and F11 are optical filters for cutting infrared light, eliminating Moire fringing, and so on. Reference numeral 18 indicates the pupil position when the magnification is low, and reference numeral 19 indicates the pupil position when the magnification is high. Detailed lens data for the optical systems used in the present embodiment is shown in Tables 10 to 14 below.

Tables 10 and 11 show one sequence of lens data, and likewise, Tables 12 and 13 show one sequence of lens data.

TABLE 10

| S | RDY | THI | Nd | Vd | ER |
|---|---|---|---|---|---|
| Obj | INF | d1 | | | |
| 1 | INF | 5.46 | | | |
| 2 | INF | 2 | 1.52287 | 59.89 | 51 |
| 3 | INF | d2 | | | 51 |
| 4 | −79.099 | 5.3 | 1.56883 | 56.36 | 51 |
| 5 | 79.099 | 5.4 | 1.7847 | 26.29 | 51 |
| 6 | 218.393 | d3 | | | 51 |
| 7 | 413.332 | 5.5 | 1.7847 | 26.29 | 51 |
| 8 | 125.21 | 9.5 | 1.497 | 81.54 | 51 |
| 9 | −125.21 | 0.2 | | | 51 |
| 10 | 433.907 | 5.7 | 1.48749 | 70.23 | 53 |
| 11 | −127.067 | 0.2 | | | 53 |
| 12 | 118.4638 | 7.26 | 1.48749 | 70.23 | 65 |
| 13 | −790.4 | 5.9871 | | | 65 |
| 14 | −60.6343 | 6.05 | 1.6134 | 44.27 | 65 |
| 15 | 99.8855 | 14.52 | 1.72 | 46.02 | 65 |
| 16 | −80.4723 | 0.605 | | | 65 |
| 17 | 74.9099 | 10.89 | 1.497 | 81.54 | 65 |
| 18 | INF | 6.05 | 1.65412 | 39.68 | 65 |
| 19 | 56.8615 | 7.0132 | | | 65 |
| 20 | 90.652 | 10.6601 | 1.48749 | 70.23 | 65 |
| 21 | −205.648 | 197.138 | | | 65 |
| 22 | 205.648 | 10.6601 | 1.48749 | 70.23 | 65 |
| 23 | −90.652 | 7.0132 | | | 65 |
| 24 | −56.8615 | 6.05 | 1.65412 | 39.68 | 60 |
| 25 | INF | 10.89 | 1.497 | 81.54 | 60 |
| 26 | −74.9099 | 0.605 | | | 60 |
| 27 | 80.4723 | 14.52 | 1.72 | 46.02 | 60 |
| 28 | −99.8855 | 6.05 | 1.6134 | 44.27 | 60 |
| 29 | 60.6343 | 5.9871 | | | 60 |
| 30 | 790.3998 | 7.26 | 1.48749 | 70.23 | 60 |
| 31 | −118.464 | 0.2 | | | 60 |
| 32 | 63.849 | 3 | 1.497 | 81.61 | 20 |

TABLE 11

| S | RDY | THI | Nd | Vd | ER |
|---|---|---|---|---|---|
| 33 | −63.849 | 2.2 | 1.72151 | 29.23 | 20 |
| 34 | −196.546 | 0.3 | | | 20 |
| 35 | 103.075 | 2.2 | 1.51633 | 64.15 | 20 |
| 36 | INF | d4 | | | 20 |
| 37 | −135.953 | 1.85 | 1.6779 | 55.33 | 16 |
| 38 | 11.911 | 3.5 | 1.71736 | 29.52 | 15 |
| 39 | 36.712 | 3.3056 | | | 15 |
| 40 | −62.029 | 1.8 | 1.6779 | 55.33 | 14 |
| 41 | 62.029 | d5 | | | 14 |
| Stop-position | INF | d6 | | | 11 |
| 43 | 118.804 | 1.7 | 1.72151 | 29.23 | 14.4 |
| 44 | 40.268 | 2.25 | 1.497 | 81.61 | 14.4 |

TABLE 11-continued

| S | RDY | THI | Nd | Vd | ER |
|---|---|---|---|---|---|
| 45 | −101.558 | 0.25 | | | 14.4 |
| 46 | 72.587 | 1.95 | 1.51633 | 64.15 | 14.2 |
| 47 | −72.587 | d7 | | | 14.2 |
| 48 | −105.657 | 1.75 | 1.6779 | 55.33 | 14 |
| 49 | 32.951 | 1.75 | 1.68893 | 31.07 | 14 |
| 50 | 105.657 | d8 | | | 14 |
| 51 | INF | 47.43 | | | |
| 52 | 29.63 | 5 | 1.58913 | 61.14 | 18 |
| 53 | −33.708 | 2.1 | 1.8044 | 39.59 | 18 |
| 54 | −83.153 | 1.1 | | | 18 |
| 55 | 15.483 | 6 | 1.497 | 81.54 | 18 |
| 56 | INF | 6.4 | 1.7725 | 49.6 | 18 |
| 57 | 10.237 | 29 | | | 18 |
| 58 | INF | 0.2 | 1.54886 | 67.84 | 11 |
| 59 | INF | 0.2 | 1.54886 | 67.84 | 11 |
| 60 | INF | 0.7 | 1.51633 | 64.14 | 11 |
| 61 | INF | 0.2 | 1.54886 | 67.84 | 11 |
| 62 | INF | 0.5 | | | 11 |
| 63 | INF | 10.093 | 1.60342 | 38.03 | 11 |
| 64 | INF | 0.3563 | | | 11 |
| 65 | INF | d9 | | | |

TABLE 12

| | | W | W | W | S | S | S |
|---|---|---|---|---|---|---|---|
| Object plane position | d1 | 200 | 300 | 500 | 200 | 300 | 500 |
| | d2 | 9.28588 | 20.2 | 30.8662 | 9.28588 | 20.2 | 30.8662 |
| | d3 | 24.24402 | 13.3299 | 2.6637 | 24.24402 | 13.3299 | 2.6637 |
| | d4 | 2.6 | 2.6 | 2.6 | 24.65 | 24.65 | 24.65 |
| | d5 | 37.93 | 37.93 | 37.93 | 15.88 | 15.88 | 15.88 |
| | d6 | 58.7 | 58.7 | 58.7 | 40.98 | 40.98 | 40.98 |
| | d7 | 2.44 | 2.44 | 2.44 | 20.15 | 20.15 | 20.15 |
| | d8 | 0 | 0 | 0 | 0 | 0 | 0 |
| | d9 | −0.00044 | −0.00044 | −0.00044 | 0.00748 | 0.00748 | 0.00748 |

TABLE 13

| | | T | T | T |
|---|---|---|---|---|
| Object plane position | d1 | 200 | 300 | 500 |
| | d2 | 9.28588 | 20.2 | 30.8662 |
| | d3 | 24.24402 | 13.3299 | 2.6637 |
| | d4 | 36.58 | 36.58 | 36.58 |
| | d5 | 3.95 | 3.95 | 3.95 |
| | d6 | 10.99 | 10.99 | 10.99 |
| | d7 | 50.15 | 50.15 | 50.15 |
| | d8 | 0 | 0 | 0 |
| | d9 | −0.00183 | −0.00183 | −0.00183 |

TABLE 14

| | Pupil position | WD | Field angle (2W) | Field of view | Image height | Magnification |
|---|---|---|---|---|---|---|
| T | 26 | 200 | 1.7° | 6.8 | 4.5 | 0.669 |
| S | 7.5 | 200 | 6° | 22 | 4.5 | 0.202 |
| W | −13.3 | 200 | 20.8° | 69 | 4.5 | 0.0669 |
| T | 26 | 300 | 1.6° | 8.9 | 4.5 | 0.5 |
| S | 7.5 | 300 | 5.5° | 29.5 | 4.5 | 0.15 |
| W | −21 | 300 | 18.5° | 91 | 4.5 | 0.05 |
| T | 26 | 400 | 1.5° | 11 | 4.5 | 0.4 |
| S | 0.82 | 400 | 5.2° | 36.5 | 4.5 | 0.123 |
| W | −29 | 400 | 17.2° | 112 | 4.5 | 0.04 |
| T | 25 | 500 | 1.4° | 13.2 | 4.5 | 0.344 |

TABLE 14-continued

| | Pupil position | WD | Field angle (2W) | Field of view | Image height | Magnification |
|---|---|---|---|---|---|---|
| S | −2.2 | 500 | 5° | 43 | 4.5 | 0.104 |
| W | −35.1 | 500 | 16.2° | 133 | 4.5 | 0.0344 |

Next, the operation of the three-dimensional medical imaging apparatus according to the present embodiment, having the above configuration, will be described.

In the same way as in the first embodiment, the surgeon places the three-dimensional medical imaging apparatus 1 and the 3D monitor 2 at a position allowing the operative site a to be observed and then carries out examination of the operative site a at low magnification, which allows the entire operative site a to be observed. Light irradiated from the light source 4 passes through the light guide 4a and illuminates the operative site a. Reflected light from the operative site a passes through the filter F11 in the image-acquisition optical system and is imaged by the objective optical system Lc4. The image of the subject (operative site a) formed by the objective optical system Lc4 is conveyed to the image-acquisition surface of the CCD by a relay optical system. The relay optical system is constructed of the collimator lens Lc5, the right-eye variable-magnification optical system La4, the left-eye variable-magnification optical system Lb4, the right-eye image-forming optical system La5, the left-eye image-forming optical system Lb5, and the filters F9a, F10a, F9b, and F10b. The collimator lens Lc5 takes incident light from the objective optical system Lc4 side and emits the incident light as an afocal beam at the CCD side. The configuration can be reduced in size by disposing the right-eye variable-magnification optical system La4 and the left-eye variable-magnification optical system Lb4 in the afocal beam produced by the collimator lens Lc5. These variable-magnification optical systems are designed to adjust the size of the image of the subject (operative site a) to be acquired by the CCD to a desired size and to emit the incident light from the objective optical system Lc4 side as an afocal beam at the CCD side. The right-eye beam emitted by the right-eye variable-magnification optical system La4 and the left-eye beam emitted by the left-eye variable-magnification optical system Lb4 are respectively imaged by the right-eye image-forming optical system La5 and the left-eye image-forming optical system Lb5 and respective images are acquired by a right-eye CCD 17a and a left-eye CCD 17b. The right-eye CCD 17a and the left-eye CCD 17b then respectively output right-eye and left-eye picture information to the CCU 5.

Based on this picture information, the surgeon performs three-dimensional examination using the 3D monitor 2. At this point, in order to dispose the three-dimensional medical imaging apparatus 1 at a distance from the operative site that allows the surgical procedure to be easily carried out in view of the position or condition of the operative site, the surgeon presses a targeting switch (not shown) to move a lens-position moving frame (not shown) by controlling a motor or the like (not shown), to change the position of the lenses L30 and L31 in the objective optical system Lc4, thus changing the focal length of the three-dimensional medical imaging apparatus 1 and bringing the operative site into focus. If the magnifications are the same, the pupil position does not change relative to the three-dimensional medical imaging apparatus 1.

Next, the surgeon proceeds with the treatment. Since the operation of the system at this point is the same as that of the first embodiment, a description thereof shall be omitted. While the surgeon is carrying out the treatment, by pressing a magnification-varying switch (not shown), the surgeon moves a lens-position-moving frame (not shown), by controlling a motor or the like, to change the position of the lenses L51a to L56a and L51b to L56b in the variable-magnification optical systems La4 and Lb4, thus magnifying the operative site. Stop members (not shown) for limiting the beams are disposed between the lenses L53a and L54a and between the lenses L53b and L54b. While magnifying the operative site, the stop members move with the lenses in the variable-magnification optical systems, and the entrance pupil positions of the image-acquisition optical systems move further away from the operative site as the magnification increases (as shown in the figure, to position 18 when the magnification is low and to position 19 when the magnification is high). Accordingly, as the magnification increases, the pupil moves closer to the entrance pupil position of the conventional surgical microscope, and perspective (meaning that distant objects are diminished and near objects are magnified) is thus reduced.

In this way, with the present embodiment it is possible to obtain perspective even when used with a variable-focal-length objective lens.

Fifth Embodiment

A fifth embodiment according to the present invention will be described with reference to FIGS. 8 to 10.

Figure 8:
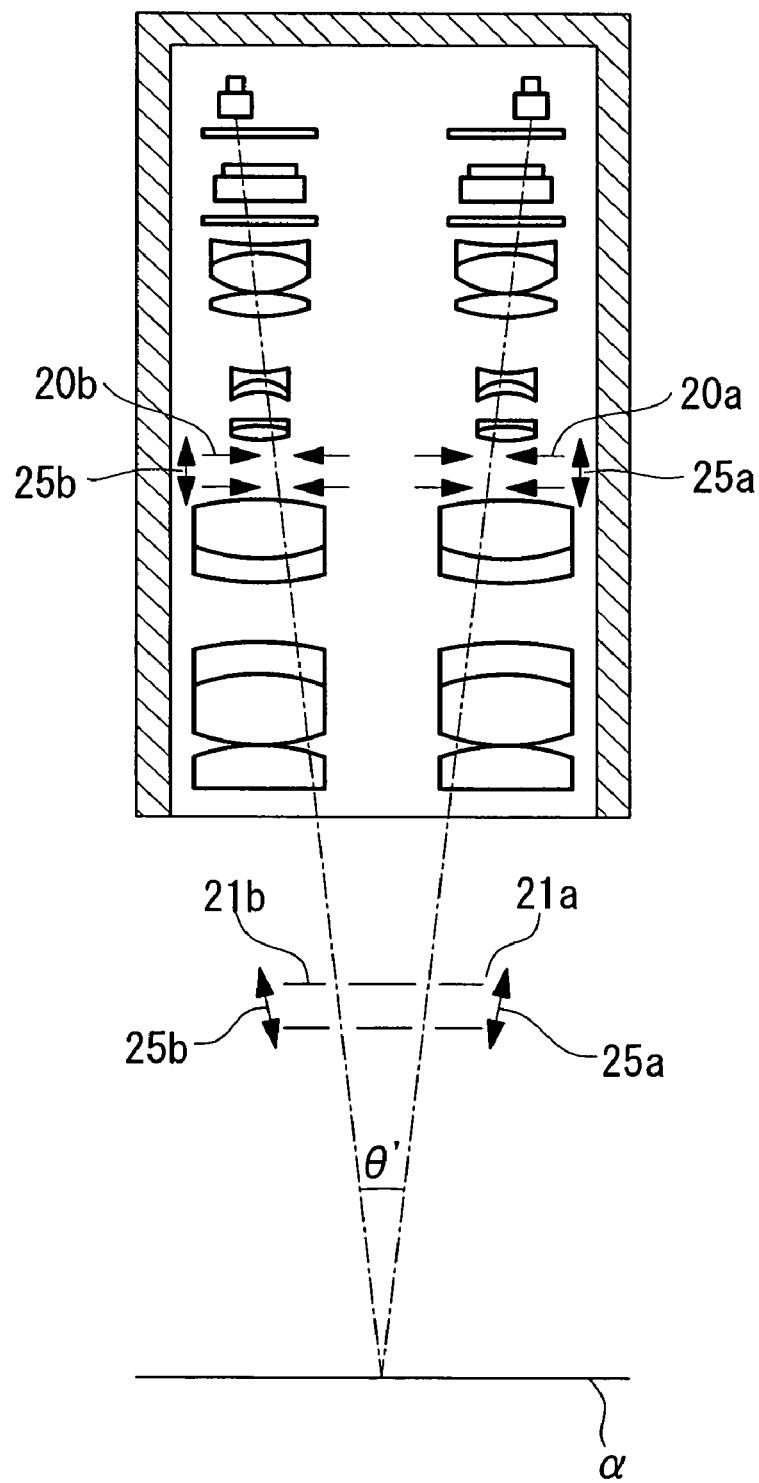
FIG. 8 is a diagram showing the configuration of an image-acquisition optical system in a three-dimensional medical imaging apparatus according to a fifth embodiment of the present invention.
Figure 9:
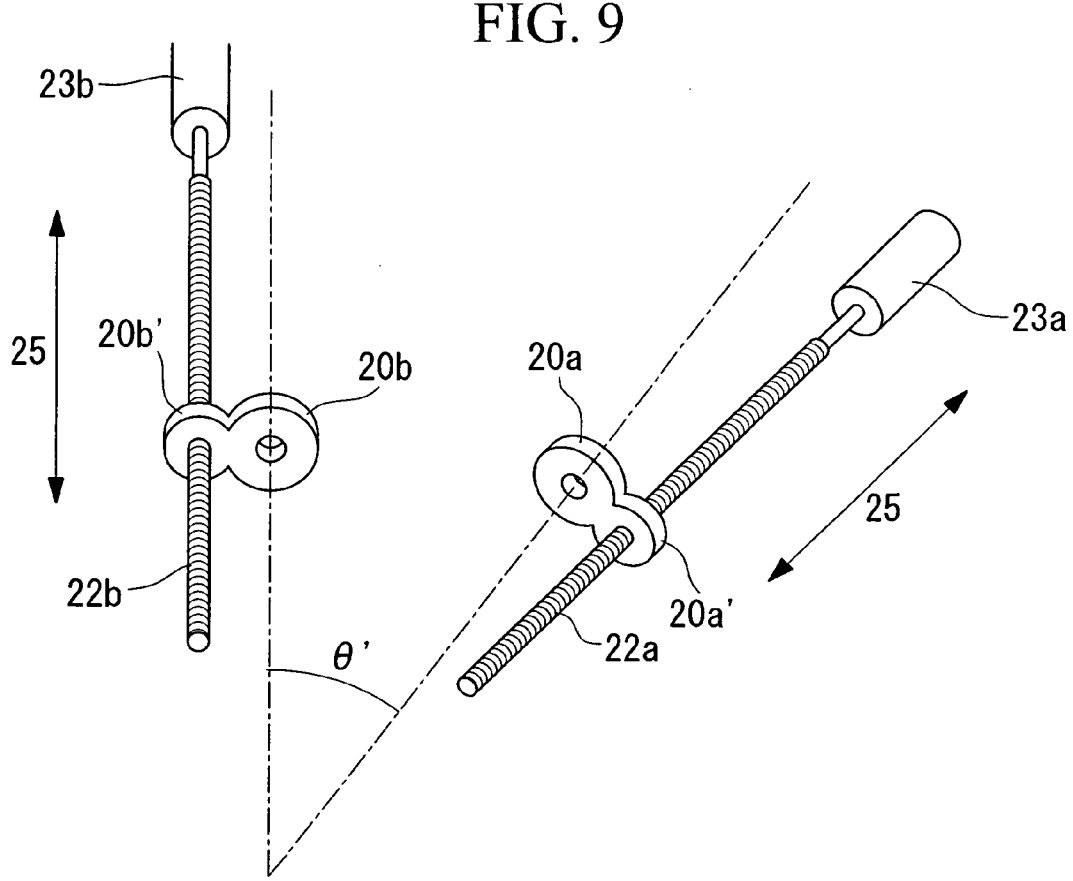
FIG. 9 is a diagram showing the configuration of a stop moving unit provided in the three-dimensional medical imaging apparatus in FIG. 8.
Figure 10:
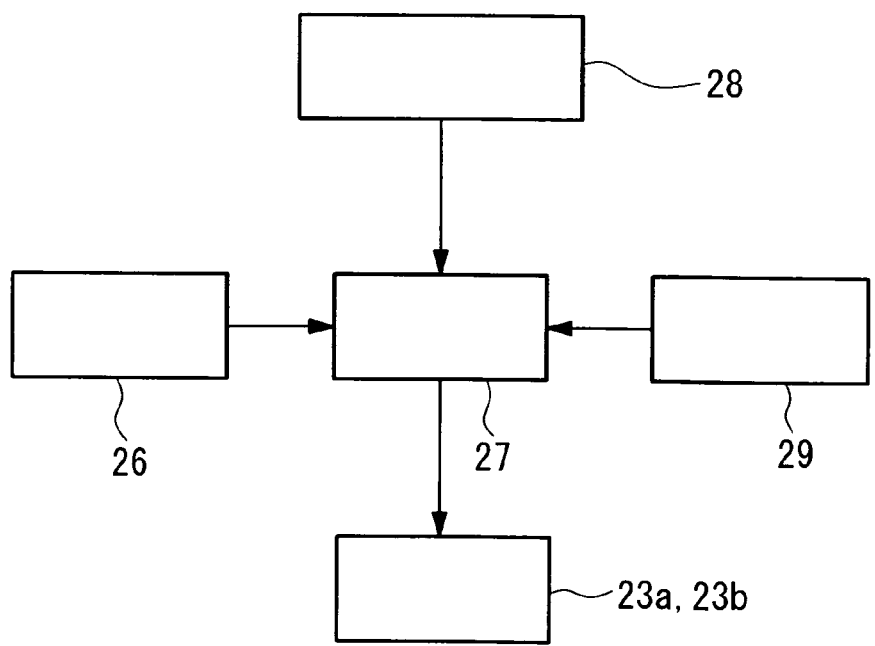
FIG. 10 is a block diagram of a stop-position control unit provided in the three-dimensional medical imaging apparatus in FIG. 8.
Figure 11:
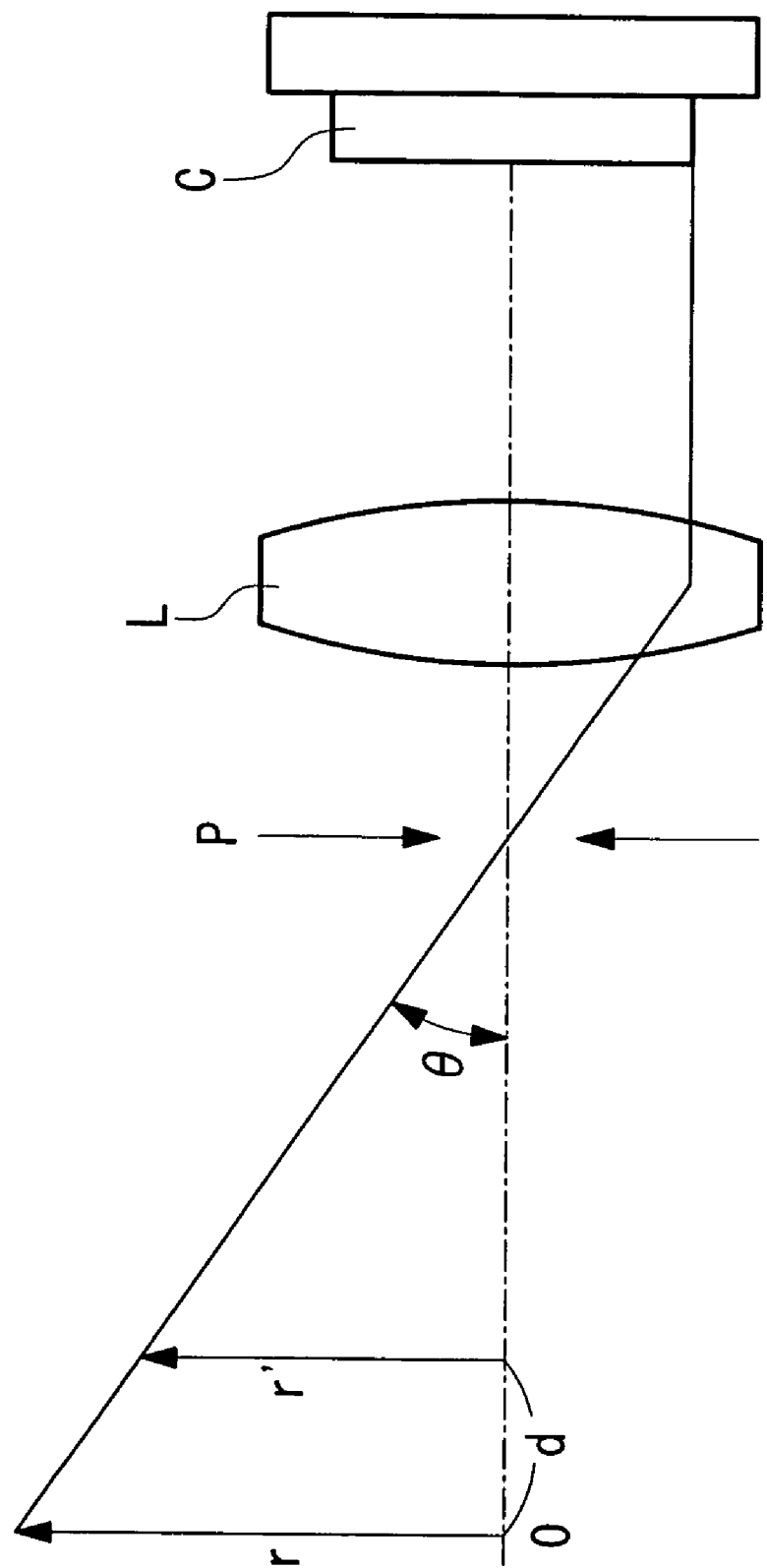
FIG. 11 is a diagram showing image acquisition of a subject using an image-acquisition unit having an image-acquisition optical system and an imaging device.
Figure 12A:
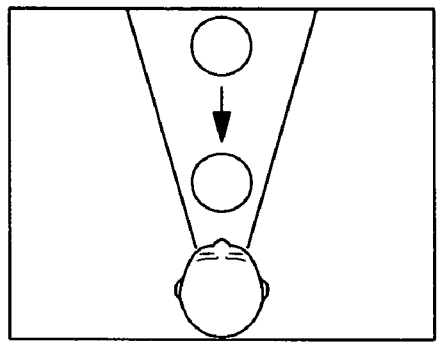
FIGS. 12A to 12C illustrate perspective when observing an object that moves in the direction of the line of sight of an observer when the field angle is small.
Figure 12B:
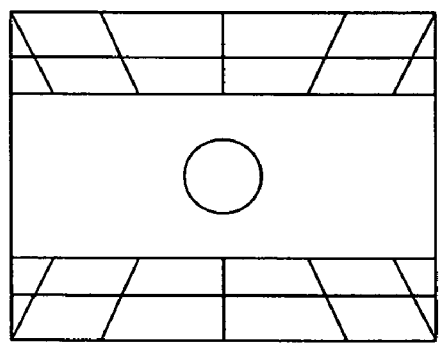
Figure 12C:
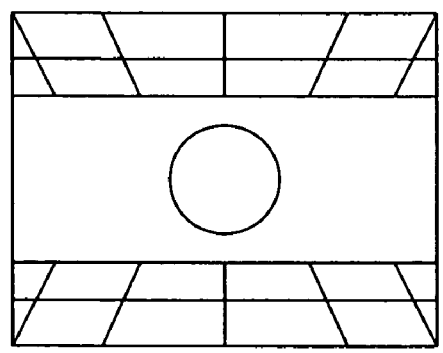
Figure 13A:
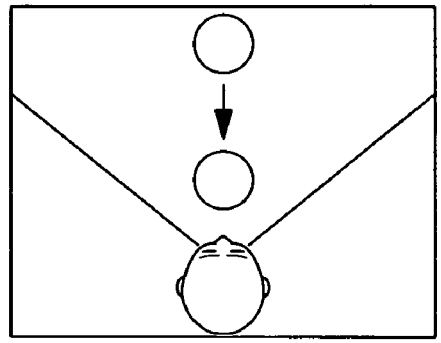
FIGS. 13A to 13C illustrate perspective when observing an object that moves in the direction of the line of sight of an observer when the field angle is large.
Figure 13B:
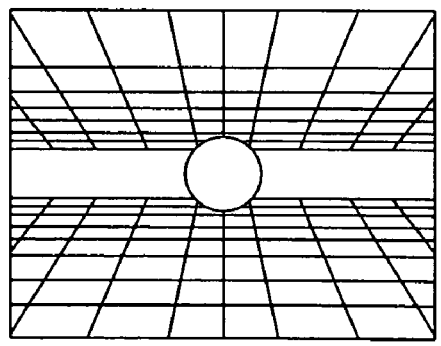
Figure 13C:
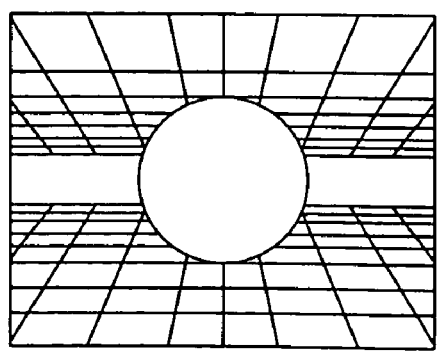

FIG. 8 is a view showing the configuration of an image-acquisition optical system in the three-dimensional medical imaging apparatus according to the present invention, FIG. 9 is a view showing the configuration of a stop moving unit provided in the three-dimensional medical imaging apparatus, and FIG. 10 is a block diagram of a stop-position control unit in the present embodiment.

The configuration of an image-acquisition optical system in the three-dimensional medical imaging apparatus will be described with reference to FIG. 8. The lens configuration of the three-dimensional medical imaging apparatus 1 of this embodiment is the same as that in the second embodiment, and therefore, a description thereof is omitted. Reference numeral 20a is a right-eye stop (stop) and reference numeral 20b is a left-eye stop (stop), and these stops define the respective pupil positions. Reference numerals 21a and 21b indicate the positions of pupils in conjugate positional relationship with respect to the pupils defined by the right-eye stop 20a and the left-eye stop 20b.

The configuration of the stop moving unit of the right-eye stop 20a and the left-eye stop 20b will be described with reference to FIG. 9. The right-eye stop 20a has a guiding thread 20a' provided in the side surface thereof, which engages with a lead screw 22a, thus enabling the right-eye stop 20a to be translated only in the screw direction 25 by a rotation-limiting mechanism (not shown). Reference numeral 23a is a motor that is connected to the lead screw 22a. Similarly, the left-eye stop 20b also has a guiding thread 20b' provided in the side surface thereof, which engages with a lead screw 22b, thus enabling the left-eye stop 20b to be translated only in the screw direction 25 by a rotation-limiting mechanism (not shown). Reference numeral 23b is a motor that is connected to the lead screw 22b. The axial directions of the right and left lead screws 22a and 22b form an internal angle $\theta'$.

The stop-position control unit will be described next with reference to FIG. 10. Reference numeral 26 is an input unit for receiving a signal input by the surgeon via a switch (not shown) for changing the stop position. The input signal is output to a control unit 27. A magnification detection unit 28 and a memory 29 are connected to the control unit 27. The motors 23a and 23b are also connected to the control unit 27.

Next, the operation of the three-dimensional medical imaging apparatus 1 according to the present embodiment, having the above configuration, will be described.

The operation of the system from the surgeon carrying out examination to changing the magnification and performing treatment is the same as that in the second embodiment, and a description thereof shall thus be omitted here.

In order to eliminate any feeling of unnaturalness in viewing the operative site, the surgeon pushes the switch (not shown). The input signal from the switch is received at the input unit 26, and that signal is transmitted to the control unit 27. The control unit 27 then outputs motor driving signals to the motors 23a and 23b to rotate the motors 23a and 23b in synchronization. When the motors 23a and 23b rotate, the lead screws 22a and 22b also rotate in synchronization therewith.

Accordingly, since the stops 20a and 20b are engaged with the lead screws 22a and 22b via the guiding threads 20a' and 20b', they move in the axial directions of the lead screws 22a and 22b, respectively, in association with the rotation of the lead screws 22a and 22b. In association with the movement of the stops, the right and left pupil positions move in the directions indicated by arrows 25a and 25b.

To provide strong perspective, the surgeon moves the stops 20a and 20b towards the subject $\alpha$ to locate the conjugate pupils 21a and 21b at the subject $\alpha$ side. Conversely, to provide weak perspective, the surgeon moves the stops 20a and 20b towards the three-dimensional medical imaging apparatus 1 to locate the conjugate pupils 21a and 21b at a position away from the subject $\alpha$.

It is possible to store a preferred position in the memory 29 in advance according to the magnification of the three-dimensional medical imaging apparatus 1. The magnification detecting unit 28 detects the magnification according to the magnification varying operation and outputs the detection result to the control unit 27. The control unit 27 compares the signal input from the magnification detection unit 28 with a signal from the memory 29 to calculate the stop position at the set magnification and outputs driving signals to the motors 23a and 23b for moving the stops to that position. Accordingly, the stop position is changed by a similar process to that described previously.

In this way, in the present embodiment, the pupils are moved by moving the stops, which allows the surgeon to set his or her preferred perspective. In synchronization with varying the magnification, by moving the stops towards the subject when the magnification is low and towards the opposite side of the subject when the magnification is high, it is possible to achieve a similar effect to that described in the third embodiment. Also, if a preferred perspective is set in advance for each magnification, it is possible to adjust the preferred perspective according to the varying magnification.

Although the same type of optical system as in the second embodiment is used in the present embodiment, the objective optical system may be of the variable-focal-length type. In such a case, when the working distance WD is long, the stop is extended towards the subject to move the pupil towards the subject, and when the working distance WD is short, the stop is moved towards CCD to move the pupils towards the CCD side, with the result that constant perspectives are obtained, regardless of the working distance WD.

What is claimed is:

1. A three-dimensional medical imaging apparatus for acquiring three-dimensional images of a subject, comprising:
   an image-acquisition optical system; and
   an imaging device,
   wherein conditional expressions (1) and (2) are satisfied $$100 \leq WD \leq 500 \qquad (1)$$

$$9° \leq 2\theta \leq 45° \qquad (2)$$

where WD is the working distance of the three-dimensional medical imaging apparatus in millimeters and θ is the half field angle of the image-acquisition optical system.

2. A three-dimensional medical imaging apparatus according to claim 1, wherein:
   the image-acquisition optical system includes
      an objective optical system for forming an image of the subject at an image-forming plane, and
      a variable-magnification optical system for adjusting the size of an image of the subject acquired by the imaging device; and
   within a range of magnifications that can be varied by the variable-magnification optical system, when at least one magnification is set, an entrance pupil position of the image-acquisition optical system is disposed between the objective optical system and the subject.

3. A three-dimensional medical imaging apparatus according to claim 1, wherein:
   the image-acquisition optical system further includes a variable-magnification optical system for adjusting the size of an image of the subject to be acquired by the imaging device; and
   within the entire range of magnifications that can be varied by the variable-magnification optical system, an entrance pupil position of the image-acquisition optical system is disposed between the objective optical system and the subject.

4. A three-dimensional medical imaging apparatus according to claim 1, wherein:
   the image-acquisition optical system further includes a variable-magnification optical system for adjusting the size of an image of the subject to be acquired by the imaging device; and
   within the entire range of magnifications that can be varied by the variable-magnification optical system, an entrance pupil position of the image-acquisition optical system is fixed at a specific position between the objective optical system and the subject.

5. A three-dimensional medical imaging apparatus for acquiring three-dimensional images of a subject, comprising:
   an image-acquisition optical system; and
   an imaging device,
   wherein the image acquisition optical system includes
      an objective optical system for forming an image of the subject at an image-forming plane, and
      a variable-magnification optical system for adjusting the size of an image of the subject acquired by the imaging device, and
   within a range of magnifications that can be varied by the variable-magnification optical system, when at least one magnification is set, conditional expressions (1) and (2) are satisfied $$100 \leq WD \leq 500 \qquad (1)$$

$$9° \leq 2\theta \leq 45° \qquad (2)$$

where WD is the working distance of the three-dimensional medical imaging apparatus in millimeters, and θ is the half field angle of the image-acquisition optical system.

6. A three-dimensional medical imaging apparatus according to claim 5, wherein the field of view on the surface of the subject in a in-focus region of the image-acquisition optical system satisfies conditional expression (3)

$$5 \leq r \leq 200 \qquad (3)$$

where r is the size in millimeters of the field of view of the image-acquisition optical system.

7. A three-dimensional medical imaging apparatus according to claim 6, wherein the field of view is defined by the effective pixel area of the imaging device.

8. A three-dimensional medical imaging apparatus for acquiring three-dimensional images of a subject, comprising:
   a pair of left and right imaging units, each imaging unit including an image-acquisition optical system and an imaging device,
   wherein the central axes of the left and right image-acquisition optical systems are disposed in parallel, and
   the left and right imaging devices are decentered with respect to the central axes the respective image-acquisition optical systems in directions such that the left and right imaging devices move away from each other.

9. A three-dimensional medical imaging apparatus according to claim 8, wherein:
   the each image-acquisition optical system includes
      an objective optical system for forming an image of the subject at an image-forming plane, and
      a variable-magnification optical system for adjusting the size of an image to be acquired by the imaging device; and
   within a range of magnifications that can be varied by the variable-magnification optical system, when at least one magnification is set, an entrance pupil position of the image-acquisition optical system is disposed between the objective optical system and the subject.

10. A three-dimensional medical imaging observation apparatus comprising a three dimensional imaging apparatus, having an image-acquisition optical system for acquiring three-dimensional images of a subject and an imaging device, and a three-dimensional display device for displaying images acquired by the three dimensional imaging apparatus, the three dimensional observation apparatus satisfying conditional expression (11) and (12) below,
   wherein, when converting the size of an image of the subject displayed on the three-dimensional display device to the field of view on the surface of the subject in the in-focus region of the image-acquisition optical system, conditional expression (13) below is satisfied $$100 \leq WD \leq 500 \qquad (11)$$

$$9° \leq 2\theta \leq 45° \quad (12)$$

$$5 \leq r \leq 200 \quad (13)$$

where WD is the working distance in millimeters of the three-dimensional medical imaging apparatus, θ is the half field angle of the medical imaging apparatus, and r is the size in millimeters of the field of view of the image-acquisition optical system.

* * * * *